US012651646B2

(12) United States Patent
Parnaby et al.

(10) Patent No.: US 12,651,646 B2
(45) Date of Patent: Jun. 9, 2026

(54) MACHINE-LEARNING MODEL FOR RECALIBRATING NUCLEOTIDE-BASE CALLS

(71) Applicant: Illumina, Inc., San Diego, CA (US)

(72) Inventors: Gavin Derek Parnaby, Laguna Niguel, CA (US); Arun Visvanath, San Diego, CA (US); Antoine Jean Dejong, Urbana, IL (US)

(73) Assignee: Illumina, Inc., San Diego, CA (US)

( * ) Notice: Subject to any disclaimer, the term of this patent is extended or adjusted under 35 U.S.C. 154(b) by 910 days.

(21) Appl. No.: 17/384,423

(22) Filed: Jul. 23, 2021

(65) Prior Publication Data

US 2023/0021577 A1     Jan. 26, 2023

(51) Int. Cl.
| | |
|---|---|
| *G16B 40/00* | (2019.01) |
| *G06N 20/00* | (2019.01) |
| *G16B 20/20* | (2019.01) |

(52) U.S. Cl.
CPC ............. *G16B 40/00* (2019.02); *G06N 20/00* (2019.01); *G16B 20/20* (2019.02)

(58) Field of Classification Search
CPC ........ G16B 40/00; G16B 20/20; G16B 30/00; G16B 40/20; G06N 20/00; G06N 3/08; G16H 50/50
See application file for complete search history.

(56) References Cited

U.S. PATENT DOCUMENTS

| | | | |
|---|---|---|---|
| 7,704,713 B2 | 4/2010 | Sato et al. | |
| 9,499,863 B2 | 11/2016 | Drmanac et al. | |
| 9,552,458 B2 | 1/2017 | White et al. | |
| 10,354,747 B1 | 7/2019 | Depristo et al. | |
| 10,600,217 B2 | 3/2020 | Kaye | |
| 11,107,554 B2 | 8/2021 | Pratt et al. | |
| 11,302,416 B2 | 4/2022 | Kermani et al. | |
| 11,527,305 B2 | 12/2022 | Kermani et al. | |
| 12,272,431 B2 | 4/2025 | DePristo et al. | |
| 2004/0002090 A1 | 1/2004 | Mayer et al. | |
| 2012/0238457 A1 | 9/2012 | Seitz et al. | |
| 2013/0110407 A1 | 5/2013 | Baccash et al. | |
| 2014/0336999 A1 | 11/2014 | Kumar et al. | |
| 2015/0292001 A1 | 10/2015 | Wiley et al. | |
| 2016/0053291 A1 | 2/2016 | Kvist et al. | |
| 2016/0232291 A1 | 8/2016 | Kyriazopoulou-Panagiotopoulou et al. | |
| 2016/0283654 A1 * | 9/2016 | Ye ......................... | G16B 30/00 |
| 2017/0191124 A1 | 7/2017 | Heredia et al. | |
| 2017/0275691 A1 | 9/2017 | Christians et al. | |
| 2017/0306392 A1 | 10/2017 | Wigler et al. | |
| 2018/0121601 A1 | 5/2018 | Hahm et al. | |
| 2018/0201916 A1 | 7/2018 | Nano | |
| 2018/0365375 A1 | 12/2018 | Flygare et al. | |
| 2019/0348152 A1 | 11/2019 | Cao | |
| 2020/0303038 A1 | 9/2020 | Luo et al. | |
| 2020/0365234 A1 | 11/2020 | Yakovenko et al. | |

| | | |
|---|---|---|
| 2021/0065847 A1 | 3/2021 | Valouev et al. |
| 2021/0257050 A1 | 8/2021 | Lam et al. |
| 2021/0257052 A1 | 8/2021 | Van Rooyen et al. |
| 2021/0295947 A1 | 9/2021 | Kyriazopoulou-Panagiotopoulou et al. |
| 2022/0199197 A1 | 6/2022 | Kermani et al. |
| 2022/0277811 A1 | 9/2022 | DePristo et al. |
| 2022/0415443 A1 | 12/2022 | Bekritski et al. |
| 2023/0021577 A1 | 1/2023 | Parnaby et al. |
| 2023/0053405 A1 | 2/2023 | Ball et al. |
| 2023/0095961 A1 | 3/2023 | Eberle |

FOREIGN PATENT DOCUMENTS

| | | |
|---|---|---|
| CN | 104232761 A | 12/2014 |
| CN | 107760771 A | 3/2018 |
| CN | 107955806 A | 4/2018 |
| GB | 2579110 A | 6/2020 |
| WO | 2002/079502 A1 | 10/2002 |
| WO | 2011/116260 A1 | 9/2011 |

(Continued)

OTHER PUBLICATIONS

O'Fallon BD. A support vector machine for identification of single-nucleotide polymorphisms from next-generation sequencing data. Bioinformatics 29(11): 1361-1366. (Year: 2013).*

Ainscough BJ. A deep learning approach to automate refinement of somatic variant calling from cancer sequencing data. Nature Genetics 50: 173501743. (Year: 2018).*

Ruibang Luo, Fritz J. Sedlazeck, Tak-Wah Lam, Michael C. Schatz; "Clairvoyante: a multi-task convolutional deep neural network for variant calling in Single Molecule Sequencing"; Posted Sep. 26, 2018; bioRxiv 310458; doi: https://doi.org/10.1101/310458; Now published in Nature Communications doi: 10.1038/s41467-019-09025-z; https://www.biorxiv.org/content/10.1101/310458v2.abstract.

(Continued)

*Primary Examiner* — Olivia M. Wise
*Assistant Examiner* — Robert J. Kallal
(74) *Attorney, Agent, or Firm* — Keller Preece PLLC

(57)     ABSTRACT

This disclosure describes methods, non-transitory computer readable media, and systems that can utilize a machine learning model to recalibrate nucleotide-base calls (e.g., variant calls) of a call-generation model. For instance, the disclosed systems can train and utilize a call-recalibration-machine-learning model to generate a set of predicted variant-call classifications based on sequencing metrics associated with a sample nucleotide sequence. Leveraging the set of variant-call classifications, the disclosed systems can further update or modify nucleotide-base calls (e.g., variant calls) corresponding to genomic coordinates. Indeed, the disclosed systems can generate an initial nucleotide-base call based on sequencing metrics for nucleotide reads of a sample sequence utilizing a call-generation model and further utilize a call-recalibration-machine-learning model to generate classification predictions for updating or recalibrating the initial nucleotide-base call from a subset of the same sequencing metrics or other sequencing metrics.

21 Claims, 12 Drawing Sheets

(56) References Cited

FOREIGN PATENT DOCUMENTS

| WO | 2014/013218 | A1 | 1/2014 |
| WO | 2017/059582 | A1 | 4/2014 |
| WO | 2015/177570 | A1 | 11/2015 |
| WO | 2016/057947 | A1 | 4/2016 |
| WO | 2020/087076 | A1 | 4/2020 |
| WO | 2020/159608 | A1 | 8/2020 |
| WO | 2022/056060 | A1 | 3/2022 |
| WO | 2022/165430 | A1 | 8/2022 |

OTHER PUBLICATIONS

Friedman S, Gauthier L, Farjoun Y, Banks E. "Lean and deep models for more accurate filtering of SNP and INDEL variant calls." Bioinformatics. Apr. 1, 2020; 36(7):2060-2067. doi: 10.1093/bioinformatics/btz901. PMID: 31830260.

Md Shariful Islam Bhuyan, Itsik Pe'er, M. Sohel Rahman "SICaRiO: Short Indel Call filteRing with bOosting"; bioRxiv 601450; doi: https://doi.org/10.1101/601450; Posted Apr. 7, 2019; Now published in Briefings in Bioinformatics doi: 10.1093/bib/bbaa238; https://www.biorxiv.org/content/biorxiv/early/2019/04/07/601450.full.pdf.

Charles Curnin, Rachel L. Goldfeder, Shruti Marwaha, Devon Bonner, Daryl Waggott, Undiagnosed Diseases Network, Matthew T. Wheeler, Euan A. Ashley, Elizabeth A. Worthey; Machine learning-based detection of insertions and deletions in the human genome; Posted May 5, 2019. bioRxiv 628222; doi: https://doi.org/10.1101/628222.

Ryan Poplin et al: "A universal SNP and small-indel variant caller using deep neural networks", Nature Biotechnology, Sep. 24, 2018 (Sep. 24, 2018), XP055572781, New York ISSN: 1087-0156, DOI: 10.1038/nbt.4235.

Alzaid Eman et al.: "PostSV: Post-Processing Approach for Filtering Structural Variations", Bioinformatics and Biology Insights, vol. 14, Jan. 1, 2020 (Jan. 1, 2020), XP093120670, NZ ISSN: 1177-9322, DOI: 10.1177/1177932219892957 Retrieved from the Internet: URL:https://journals.sagepub.com/doi/pdf/10.1177/1177932219892957.

"BLAT Search Genome," webpage <https://genome.ucsc.edu/cgi-bin/hgBlat>, 1 page, Apr. 12, 2002, retrieved on Feb. 27, 2024.

"Deeper insights into complex regions of the genome," webpage <https://www.illumina.com/science/technology/next-generation-sequencing/long-read-sequencing.html>, 4 pages, retrieved on Feb. 23, 2024.

Illumina, "High-performance long-read assay enables contiguous data with N50 of 6-7 kb on existing Illumina platforms," webpage <https://www.illumina.com/science/genomics-research/articles/infinity-high-performance-long-read-assay.html>, 6 pages, Sep. 29, 2022, retrieved on Feb. 23, 2024.

J.M. Catchen et al: "Stacks: Building and Genotyping Loci De Novo From Short-Read Sequences", G3: Genes/Genomes/Genetics, vol. 1, No. 3, Aug. 1, 2011 (Aug. 1, 2011), pp. 171-182, XP055071071, DOI: 110.1534/g3.111.000240.

Ke Ziqi Ziqike@Utexas edu et al: "Deep learning for assembly of haplotypes and viral quasispecies from short and long sequencing reads", Proceedings of the 36th IEEE/ACM International Conference on Automated Software Engineering, ACMPUB27, New York, NY, USA, Aug. 7, 2022 (Aug. 7, 2022), pp. 1-10, XP058907477, DOI: 10.1145/3535508.3545524 ISBN: 978-1-4503-9442-0.

Lal Gupta Chhedi et al: "Platforms for elucidating antiobotic resistance in single genomes and complex metagenomes", Environment International, Pergamon Press, US, vol. 138, Mar. 29, 2020 (Mar. 29, 2020), XP086116224, ISSN: 0160-4120, DOI: 10.1016/J.ENVINT.2020.105667 [retrieved on Mar. 29, 2020].

Narasimhan Vagheesh et al: BCFtools/RoH: a hidden Markov model approach for detecting autozygosity from next-generation sequencing data, Bioformatics, vol. 32, No. 11, Jan. 30, 2016 (Jan. 30, 2016), pp. 1749-1751, XP055785146, GB ISSN: 1367-403, DOI: 10.1093/bioformatics/btw044 Retrievced from the Internet: URL:https://www.ncbi.nlm.nih.gov/pmc/articles/PMC4892413/pdf/btw044.pdf.

Nielsen R, Paul JS, Albrechtsen A, Song YS. Genotype and SNP calling from next-generation sequencing data. Nat Rev Genet. Jun. 2011;12(6):443-51. doi: 10.1038/nrg2986. PMID: 21587300; PMCID: PMC3593722.

Shafin Kishwar et al: "Haplotype-aware variant calling with PEPPER-Margin-DeepVariant enables high accuracy in a nanopore long-reads", Nature Methods, Nature Publishing Group US, New York, vol. 18, No. 11, Nov. 1, 2021 (Nov. 1, 2021), pp. 1322-1332, XP037608949, ISSN: 1548-7094, DOI: 1038/S41592-021-01299-W [retrieved on Nov. 1, 2021].

"The variant call format specification," Nov. 27, 2022, 37 pages, VCFv4.3 and BCFv2.2.

Wikipedia, The Free Encyclopedia. "Nanopore sequencing." Website: <https://en.wikipedia.org/wiki/Nanopore_sequencing>. 12 Pages. Last edited Dec. 11, 2023.

A. Acha-Sagredo et al: "Somatic variation in normal tissues: friend or foe of cancer early detection?", ScienceDirect, Annals of Oncology, Dec. 2022, vol. 33, Issue 12, pp. 1239-1249, https://doi.org/10.1016/j.annonc.2022.09.156.

August Yue Huang et al: "MosaicHunter: accurate detection of postzygotic single-nucleotide mosaicism through next-generation sequencing of unpaired, trio, and paired samples". Nucleic Acids Res. Jan. 28, 2017, vol. 45(10):e76. doi: 10.1093/nar/gkx024, 13 pgs.

Derek Caetano-Anolles, "Variant Quality Score Recalibration (VQSR), GATK Technical Documentation", webpage <https://gatk.broadinstitute.org/hc/en-us/categories/360002310591-Technical-Documentation>, 3 pages, retrieved on Mar. 14, 2024.

Krystyna Wasilewska et al. "Postzygotic mutations and where to find them—Recent advances and future implications in the field of non-neoplastic somatic mosaicism", ScienceDirect—Mutation Research/Reviews in Mutation Research, Jun. 9, 2022, vol. 790, https://doi.org/10.1016/j.mrrev.2022.108426, 13 pgs.

L. Van Horebeek, et al: "Somatic Variants: New Kids on the Block in Human Immunogenetics", Cell Press Reviews—Trends in Genetics, Oct. 24, 2019, vol. 35, No. 12 https//doi.org/10.1016/j.tig.2019.09.005, 935-947.

Ryan. F. McCormick et al: RIG: Recalibration and Interrelation of Genomic Sequence Data with the GATK, G3 Genes|Genomes|Genetics, vol. 5, Issue 4, Apr. 1, 2015, pp. 655-665, https://doi.org/10.1534/g3.115.017012.

Satoshi Oota. "Somatic mutations—Evolution within the individual", ScienceDirect, Methods, Apr. 1, 2020, vol. 176, pp. 91-98, https://doi.org/10.1016/j.ymeth.2019.11.002.

Yifan Wang et al: "Comprehensive identification of somatic nucleotide variants in human brain tissue", Genome Biology, Mar. 29, 2021, Article No. 92, https://doi.org/10.1186/s13059-021-02285-3, 32 pgs.

Bentley, et al. Accurate whole human genome sequencing using reversible terminator chemistry, Nature, vol. 456, Nov. 6, 2008, pp. 53-59, including supplemental information pp. 1-55, doi: 10.1038/nature07517.

Cameron, et al. Gridss: Sensitive And Specific Genomic Rearrangement Detection Using Positional De Bruijn Graph Assembly, Genome Research, vol. 27, 2017, 2050-2060. doi: 10.1101/gr.222109.117.

Can Alkan et al., "Genome structural variation discovery and genotyping", Nat Rev Genet. May 2011;12(5):363-76. doi: 10.1038/nrg2958.

Choi, et al. The use of modified and non-natural nucleotides provide unique insights into pro-mutagenic replication catalyzed by polymerase eta, Nucleic Acids Research, pp. 1022-1035, Dec. 29, 2015. DOI: 10.1093/nar/gkv1509.

Cochran, D. et al., Sequencing by Aligning Mutated DNA Fragments (SAM), In: Xing, WL., Cheng, J. (eds) Frontiers in Biochip Technology. Springer, Boston, MA. pp 231-245, 2006, https://doi.org/10.1007/0-387-25585-0_15.

Elshawadfy, Ashraf M., et al. DNA polymerase hybrids derived from the family-B enzymes of Pyrococcus furiosus and Thermococcus kodakarensis: improving performance in the polymerase chain reaction, frontiers in Microbiology, May 27, 2014, 14 pages.

(56)             References Cited

OTHER PUBLICATIONS

Harris, et al. The Effect of Tautomeric Constant on the Specificity of Nucleotide Incorporation during DNA Replication: Support for the Rare Tautomer Hypothesis of Substitution Mutagenesis, J. Mol. Biol. (2003) 326, 1389-1401, Aug. 24, 2015. https://doi.org/10.1016/S0022-2836(03)00051-2.

Hsu, et al. Error-Prone Replication Of Oxidatively Damaged DNA By A High-Fidelity DNA Polymerase, Nature, vol. 431, 217-221, Sep. 2004.

Jacob Durtschi et al: "VarBin, a novel method for classifying true and false positive variants in NGS data", Bmc Bioinformatics, Biomed Central, London, GB, vol. 14, No. Suppl 13, Oct. 1, 2013 (Oct. 1, 2013), p. S2, XP021162994, ISSN: 1471-2105, DOI: 10.1186/1471-2105-14-S13-S2.

Keith, et al. A simulated annealing algorithm for finding consensus sequences, Bioinformatics, vol. 18, No. 11, 2002, p. 1494-1499, Nov. 1, 2002. https://doi.org/10.1093/bioinformatics/18.11.1494.

Keith, et al. Algorithms for Sequence Analysis via Mutagenesis, Bioinformatics, vol. 20 No. 15; 2401-2410, May 14, 2004. published online doi: 10.1093/bioinformatics/bth258.

Keith, et al. Chapter 10 Sequencing Aided by Mutagenesis Facilitates the De Novo Sequencing of Megabase DNA Fragments by Short Read Lengths, Perspectives in Bioanalysis, vol. 2, pp. 303-326, 2007. https://doi.org/10.1016/S1871-0069(06)02010-6.

Keith, et al. Unlocking Hidden Genomic Sequence, Nucleic Acids Research, vol. 32, No. 3, e35, Feb. 18, 2004. published online DOI: 10.1093/nar/gnh022.

Kuwahara, et al. Study on suitability of KOD DNA polymerase for enzymatic production of artificial nucleic acids using base/sugar modified nucleoside triphosphates, Molecules, 8229-8240, Nov. 12, 2010. https://doi.org/10.3390/molecules15118229.

Levy, et al. Facilitated sequence counting and assembly by template mutagenesis, PNAS, vol. 111, No. 43, Oct. 13, 2014, E4632-E4637.

Lin, et al. Synthesis and duplex stability of oligonucleotides containing cytosine-thymine analogues, Nucleic Acids Research, 17(24), Dec. 25, 1989, 10373-10383. doi: 10.1093/nar/17.24.10373.

Mark a Depristo et al: "A framework for variation discovery and genotyping using next-generation DNA sequencing data", Nature Genetics, vol. 43, No. 5, Jan. 1, 2011 (Jan. 1, 2011), pp. 491-498, XP055046798, ISSN: 1061-4036, DOI: 10.1038/ng.806.

Maxam, et al. A new method for sequencing DNA, PNAS USA, 1977, 560-564.

Moore, et al. Direct Observation of Two Base-pairing Modes of a Cytosine-Thymine Analogue with Guanine in a DNAZ-form Duplex: Significance for Base Analogue Mutagenesis, Journal of Molecular Biology, vol. 251, Issue 5, pp. 665-673, Aug. 1, 1995. https://doi.org/10.1006/jmbi.1995.0463.

Narzisi, G., et al. Scoring-and-unfolding trimmed tree assembler: concepts, constructs and comparisons, Bioinformatics 27.2, Nov. 18, 2010, 153-160. doi: 10.1093/bioinformatics/btq646.

Nedderman, et al. Molecular Basis for Methoxyamine-initiated Mutagenesis: 1H Nuclear Magnetic Resonance Studies of Oligonucleotide Duplexes Containing Base-modified Cytosine Residues, Journal of Molecular Biology, vol. 230, Issue 3, pp. 1068-1076, Apr. 5, 1993. https://doi.org/10.1006/jmbi.1993.1219.

Petrie, et al. Deep sequencing analysis of mutations resulting from the incorporation of dNTP analogs, Nucleic Acids Research, vol. 38, Issue 22, 8095-8104, Dec. 1, 2010. https://doi.org/10.1093/nar/gkq685.

Sanger, F., et al. A Rapid Method for Determining Sequences in DNA by Primed Synthesis with DNA Polymerase, J. Mol. Biol. 94, 441-448, 1975. doi: 10.1016/0022-2836(75)90213-2.

Shen. PCR Approaches to DNA Mutagenesis and Recombination—An Overview, Methods in Molecular Biology, vol. 192. pp 167-174, 2002. DOI: 10.1385/1-59259-177-9:167.

Sipos, et al. An Improved Protocol for Sequencing of Repetitive Genomic Regions and Structural Variations Using Mutagenesis and Next Generation Sequencing, PLoS One 7(8), e43359, published online Aug. 17, 2012, doi: 10.1371/journal.pone.0043359.

Sladitschek, et al. MorphoSeq: Full Single-Cell Transcriptome Dynamics Up to Gastrulation in a Chordate, Cell, 922-935, May 14, 2020.

Stone, et al. Molecular asis for Methoxyamine Initiated Mutagenesis: 1H Nuclear Magnetic Resonance Studies of Base-modified Oligodeoxynucleotides, Journal of Molecular Biology, vol. 222, Issue 3, pp. 711-723, Dec. 5, 1991. https://doi.org/10.1016/0022-2836(91)90507-3.

Supek, et al. Clustered Mutation Signatures Reveal that Error-Prone DNA Repair Targets Mutations to Active Genes, Cell, vol. 170, 534-547, Jul. 27, 2017.

Yamashita, et al. Characterization of Recombinant Thermococcus kodakaraensis (KOD) DNA Polymerases Produced Using Silkworm-Baculovirus Expression Vector System, Molecular Biotechnology vol. 59, pp. 221-233, Jun. 2017. DOI: 10.1007/s12033-017-0008-9.

Zaccolo, et al. An Approach to Random Mutagenesis of DNA Using Mixtures of Triphosphate Derivatives of Nucleoside Analogues, Journal of Molecular Biology, Feb. 2, 1996, 589-603.

Zinger, et al. Assessment of Microbial Communities by Graph Partitioning in a Study of Soil Fungi in Two Alpine Meadows, Applied and Environmental Microbiology, vol. 75, No. 18, 5863-5870, Sep. 2009.

Anonymous: "The Variant Call Format (VCF) Version 4.1 Specification", Dec. 17, 2013, XP093221724.

Derek Caetano-Anolles, Variant Quality Score Recalibration (VQSR), GATK Technical Documentation, Webpage <https://gatk.broadinstitute.org/hc/en-us/articles/360035531612-Variant-Quality-Score-Recalibration-VQSR->, 13 pages, Sep. 30, 2022, retrieved from the Internet Wayback Machine <https://web.archive.org/web/20221206173630/https://gatk.broadinstitute.org/hc/en-us/articles/360035531612-Variant-Quality-Score-Recalibration-VQSR-> on Sep. 23, 2024.

Adamewing. bamsurgeon. Github. 2016. Last updated Oct. 18, 2024. 4 pages, [Retrieved from the Internet on May 14, 2025] <URL: https://github.com/adamewing/bamsurgeon>.

Charlotte A. Darby et al., Samovar: Single-Sample Mosaic Single-Nucleotide Variant Calling with Linked Read, iScience 29;18, pp. 1-10, May 2019, doi: 10.1016/j.isci.2019.05.037.

Erik Garrison et al. "Variation Graph Toolkit Improves Read Mapping by Representing Genetic Variation in the Reference", Nature Biotechnology. 36(9) pp. 875-879. Oct. 2018. https://www.ncbi.nlm.nih.gov/pmc/articles/PMC6126949/.

Goran Rakocevic et al. "Fast and Accurate Genomic Analyses using Genome Graphs", Nature Genetics 51, pp. 354-362, Jan. 2019. https://doi.org/10.1038/s41588-018-0316-4.

Haoyu Cheng et al. "Haplotype-Resolved Assembly of Diploid Genomes without Parental Data", Nature Biotechnology, 40, pp. 1332-1335, Mar. 2022. https://doi.org/10.1038/s41587-022-01261-x.

Sarah E. Jensen et al. "A Sorghum Practical Haplotype Graph Facilitates Genome-Wide Imputation and Cost-Effective Genomic Prediction," The Plant Genome 13 (1) 15 pages, Mar. 2020. https://pubmed.ncbi.nlm.nih.gov/33016627/.

Shuai Yuan et al., "One Size Doesn't Fit All—RefEditor: Building Personalized Diploid Reference Genome to Improve Read Mapping and Genotype Calling in Next Generation Sequencing Studies," PLoS Computational Biology 11(8): e1004448, 15 pages, Aug. 2015. https://doi.org/10.1371/journal.pcbi.1004448.

Shuai Yuan and Zhohui Qin. "Read Mapping Using Personalized Diploid Reference Genome for RNA Sequencing Data Reduced Bias for Detecting Allele-Specific Expression," 2012 IEEE International Conference on Bioinformatics and Biomedicine Workshops. IEEE, pp. 718-724, Oct. 2012. https://ieeexplore.ieee.org/abstract/document/6470225.

Xiaoxu Yang et al., "Control-Independent Mosaic Single Nucleotide Variant Detection with DeepMosaic", Nature Biotechnology 41, pp. 870-877, Jan. 2023, https://doi.org/10.1038/s41587-022-01559-w.

Yanmei Dou et al., "Accurate Detection of Mosaic Variants in Sequencing Data without Matched Controls". Nature Biotechnology 38(3), pp. 314-319, Mar. 2020, doi: 10.1038/s41587-019-0368-8.

(56) References Cited

OTHER PUBLICATIONS

Yoo-Jin Ha et al., "A Robust Benchmark for Evaluating and Improving Mosaic Variant Calling Strategies", 25 pages, Sep. 2021, doi: https://doi.org/10.21203/rs.3.rs-871399/v1.

Yoo-Jin Ha et al., "Establishment of Reference Standards for Multifaceted Mosaic Variant Analysis", Scientific Data 9:35, 10 pages 2022, https://doi.org/10.1038/s41597-022-01133-8.

Peter Andolfatto et al. "Multiplexed Shotgun Genotyping for Rapid and Efficient Genetic Mapping", Genome Research, 21:610-617, 2011.

Anand Ramachandran, Lumetta, S.S., Klee, E.W et al. HELLO: improved neural network architectures and methodologies for small variant calling. BMC Bioinformatics 22:404, pp. 1-31, (Year: 2021).

David Heller, Martin Vingron, SVIM-asm: structural variant detection from haploid and diploid genome assemblies, Bioinformatics, vol. 36, Issue 22-23, Dec. 2020, pp. 5519-5521, (Year: 2020).

* cited by examiner

| SNP Type 2 Stats at Best F-Measure Point | | | | | | | | | | |
|---|---|---|---|---|---|---|---|---|---|---|
| ID | Tagname | Qual | TP | FN | FP | Hethom | Vardiff | FP+FN | Recall | Precision | F-Measure |
| 23987 | Recalibrated Model | 3.00000 | 3317594 | 9656 | 4073 | 1660 | 9 | 13729 | 0.997098 | 0.998774 | 0.997935 |
| 23740 | Non-Recalibrated Model | 4.00000 | 3315720 | 11530 | 6927 | 2667 | 9 | 18456 | 0.996535 | 0.997915 | 0.997225 |

Best Stats

Non SNP ROC

706

708

INDEL Type 2 Stats at Best F-Measure Point

| ID | Tagname | Qual | TP | FN | FP | Hethom | Vardiff | FP+FN | Recall | Precision | F-Measure |
|---|---|---|---|---|---|---|---|---|---|---|---|
| 23987 | Recalibrated Model | 4.00000 | 503156 | 1588 | 998 | 651 | 50 | 2586 | 0.996854 | 0.998020 | 0.997437 |
| 23740 | Non-Recalibrated Model | 3.00000 | 503171 | 1574 | 1342 | 749 | 52 | 2915 | 0.996883 | 0.997341 | 0.997112 |

Best Stats

Determining Sequencing Metrics For Nucleotide-Base Calls 902

Generating Variant-Call Classifications Based On The Sequencing Metrics 904

Determining A Final Nucleotide-Base Call Based On The Variant-Call Classifications 906

MACHINE-LEARNING MODEL FOR RECALIBRATING NUCLEOTIDE-BASE CALLS

BACKGROUND

In recent years, biotechnology firms and research institutions have improved hardware and software for sequencing nucleotides and determining nucleotide-base calls (e.g., variant calls) for genomic samples. For instance, some existing nucleotide-base-sequencing platforms determine individual nucleotide bases within sequences by using conventional Sanger sequencing or by using sequencing-by-synthesis (SBS). When using SBS, existing platforms can monitor many thousands of nucleic-acid polymers being synthesized in parallel to predict nucleotide-base calls from a larger base-call dataset. For instance, a camera in many SBS platforms captures images of irradiated fluorescent tags incorporated into oligonucleotides for determining the nucleotide-base calls. After capturing such images, existing SBS platforms send base-call data (or image data) to a computing device to apply sequencing-data-analysis software that determines a nucleotide-base sequence for a nucleic-acid polymer. In certain cases, some prior systems further utilize a variant caller to identify variants, such as single nucleotide polymorphisms (SNPs), insertions or deletions (indels), or other variants within a sample's nucleic-acid sequence.

Despite these recent advances in sequencing and variant calling, existing sequencing-data-analysis software often include variant callers that identify excessive numbers of false positives and false negatives. For example, in some circumstances, existing software applies a variant caller that falsely identifies excessive numbers of variants at sites or coordinates without such variants within a reference sequence. As another example, existing variant callers often mistakenly identify excessive numbers of non-variant subsequences in a sample sequence at sites or coordinates where the sample sequence includes actual variants that differ from references bases of a reference sequence. Indeed, existing variant callers achieve a certain level of accuracy but, due to their limitations, still leave room for improvement in reducing false positives and recovering false negatives. For example, a variant call identifying a particular single nucleotide polymorphism (SNP) in the hemoglobin beta (HBB) gene can have significant implications. When a variant caller identifies an SNP at rs344 on chromosome 11, for instance, the variant caller can either correctly identify the genetic cause of sickle cell anemia or miss the cause of the disease. As a further example, a variant call that correctly or incorrectly identifies the deletion of one or more copies of hemoglobin subunit alpha 1 (HbA1) or hemoglobin subunit alpha 2 (HbA2) genes can result in either correctly identifying a genetic cause of an inherited blood disorder or miss the gene deletion entirely.

As a contributing factor to the aforementioned inaccuracies, many existing nucleotide-base-sequencing platforms and sequencing-data-analysis software (together and hereinafter, existing sequencing systems) leverage only limited sets of data in determining nucleotide-base calls. For instance, existing sequencing systems frequently rely exclusively on information extracted directly from nucleotide reads of a sample sequence, such as read depth, mismatch counts, and mapping quality, to determine nucleotide-base calls. While sequence information from nucleotide reads can provide valuable insight for determining nucleotide-base calls, existing systems that solely rely on these data can underperform when it comes to accurately determining nucleotide-base calls. Indeed, some existing sequencing systems that rely on raw sequence data incorrectly determine SNPs, indels, or other variants in a sample sequence in comparison to more complex models. Indeed, existing sequencing systems frequently identify false negative variants or false positive variants in the Truth Challenges of the U.S. Food and Drug Administration (FDA).

In addition to inaccurately determining variant calls, some existing sequencing systems also inefficiently expend computing resources with overly complex models. Specifically, the variant callers of some existing sequencing systems are computationally expensive and slow. Indeed, some existing systems utilize variant callers with a deep learning architecture or some other neural network architecture that require extensive computational resources (e.g., computing time, processing power, and memory) to train and apply. For example, some existing systems utilize deep learning architectures that, even after training, take many hours across multiple computing devices to generate nucleotide-base calls for a single sample sequence.

As an added drawback of existing sequencing systems with complex networks, many such systems utilize model architectures that render sequence data uninterpretable. More specifically, some existing deep neural networks transform and manipulate the sequence data many times over, changing from one vector to another across the various layers and neurons, as the basis for generating a variant call. In many cases, the internal data of these deep neural networks is uninterpretable and impossible to utilize in any way outside of the neural network architecture itself.

SUMMARY

This disclosure describes embodiments of methods, non-transitory computer readable media, and systems that can utilize a machine learning model to recalibrate nucleotide-base calls (e.g., variant calls) of a call-generation model. For example, the disclosed systems can train and utilize a call-recalibration-machine-learning model to generate a set of classification predictions (e.g., variant-call classifications) from sequencing metrics associated with a sample nucleotide sequence. Leveraging the set of classification predictions, the disclosed systems can further update or modify nucleotide-base calls for the sample sequence. Indeed, the disclosed systems can i) generate an initial nucleotide-base call (e.g., an initial variant call) with respect to a genomic coordinate of a reference genome based on sequencing metrics for nucleotide reads of a sample sequence utilizing a call-generation model and (ii) utilize a call-recalibration-machine-learning model to generate classification predictions for updating or recalibrating the initial nucleotide-base call from a subset of the same sequencing metrics. After recalibrating, the disclosed systems can output the updated or recalibrated nucleotide-base call as a final nucleotide-base call (e.g., a final variant call) in a variant call file or other base-call-output file.

By utilizing a call-recalibration-machine-learning model to update sequencing metrics for generating nucleotide-base calls, the disclosed systems can improve accuracy, efficiency, and speed over existing sequencing systems. As described further below, for instance, the disclosed call-recalibration-machine-learning model determines variant calls with better accuracy and faster computing times than more complex neural networks for variant calling. Additionally, the disclosed systems can improve interpretability of factors impacting accurate variant calls by utilizing a callrecalibration-machine-learning model that processes data in an accessible, interpretable format. Indeed, because of the improved interpretability of the disclosed systems, in some embodiments, the disclosed systems can generate and provide a visualization of various contribution measures associated with individual sequencing metrics to visually depict respective measures of impact that the sequencing metrics have on a resultant nucleotide-base call.

BRIEF DESCRIPTION OF THE DRAWINGS

The detailed description refers to the drawings briefly described below.

DETAILED DESCRIPTION

Figure 1:
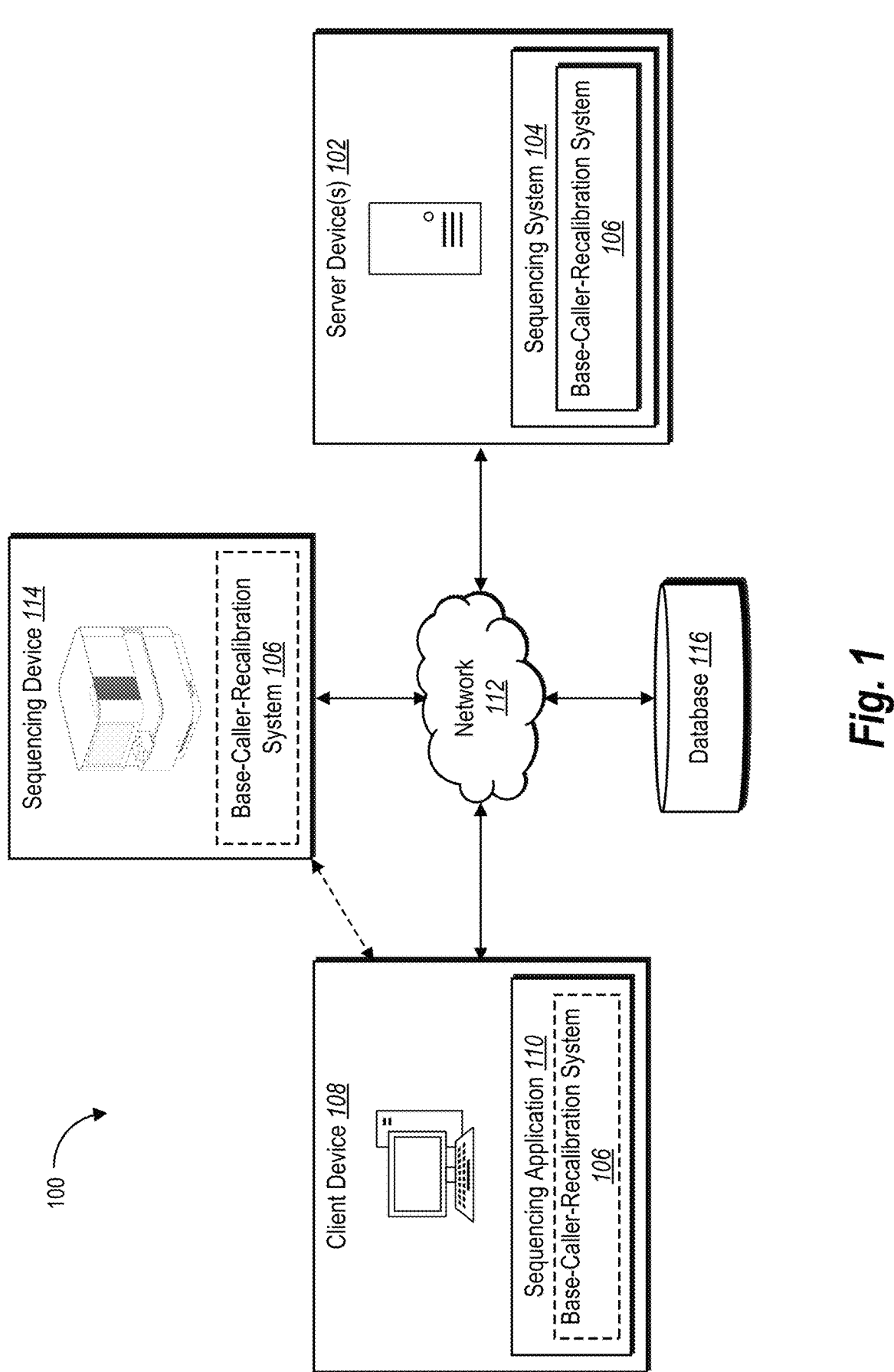
FIG. 1 illustrates a block diagram of a sequencing system including a base-caller-recalibration system in accordance with one or more embodiments.

This disclosure describes embodiments of a base-caller-recalibration system that generates and recalibrates nucleotide-base calls for a sample nucleotide sequence utilizing a call-generation model and a call-recalibration-machine-learning model. In particular, the base-caller-recalibration system can utilize a call-generation model to generate an initial nucleotide-base call (e.g., a base call identifying a variant call or a non-variant call with respect to a reference genome) from sequencing metrics identified or obtained from nucleotide reads of a sample nucleotide sequence. In addition, the base-caller-recalibration system can recalibrate the initial nucleotide-base call to improve its accuracy by utilizing a call-recalibration-machine-learning model to update various call metrics such as a call quality, a genotype associated with the call, and/or a genotype quality associated with the genotype. By utilizing the call-recalibration-machine-learning model to update metrics, the base-callerrecalibration system can remove false positives from nucleotide-base calls of the sample nucleotide sequence and/or can recover false negatives from nucleotide-base calls of the sample nucleotide sequence.

As just mentioned, in certain implementations, the base-caller-recalibration system extracts or determines sequencing metrics from a sample nucleotide sequence. For example, the base-caller-recalibration system determines sequencing metrics from nucleotide-base calls of nucleotide reads from a sample nucleotide sequence. Indeed, in some cases, the base-caller-recalibration system generates or determines a set of nucleotide-base calls from nucleotide reads captured or determined via fluorescent imaging of a sample nucleotide sequence (e.g., at a particular genomic coordinate). From the read-based nucleotide-base calls, in some embodiments, the base-caller-recalibration system determines or extracts various sequencing metrics (e.g., sequencing metrics of various types obtained from reads and/or from different components of a call-generation model).

To elaborate, in certain implementations, the base-caller-recalibration system determines different types of sequencing metrics associated with different sources. For example, the base-caller-recalibration system determines read-based sequencing metrics including metrics derived from nucleotide reads of the sample nucleotide sequence. In addition, the base-caller-recalibration system determines externally sourced sequencing metrics identified from one or more external databases that indicate various nucleotide attributes, mapping challenges, and genomic sequences associated with sequencing biases. Further, the base-caller-recalibration system determines call-model-generated sequencing metrics generated via a variant caller or other call-generation model, such as variables internal to the base-caller-recalibration system that are not accessible to other systems or parties (e.g., proprietary quality scores, base contexts, read filtering, proprietary hypothesis scores, and other metrics). Indeed, in some cases, the base-caller-recalibration system determines call-model-generated sequencing metrics in the form of variant-calling sequencing metrics and mapping-and-alignment sequencing metrics, where each type is extracted by different components of the call-generation model.

As further mentioned, in certain implementations, the base-caller-recalibration system generates a set of predicted classifications from the sequencing metrics for modifying or improving a nucleotide-base call or variant-call data or fields associated with a nucleotide-base call. More specifically, the base-caller-recalibration system utilizes a call-recalibration-machine-learning model to generate, from the sequencing metrics, a set of three variant-call classifications that impact or reflect the accuracy of identifying a variant at a particular genomic coordinate (e.g., a genomic coordinate corresponding to nucleotide-base calls of nucleotide reads from a sample nucleotide sequence). For instance, the base-caller-recalibration system utilizes the call-recalibration-machine-learning model to generate variant-call classifications including: i) a false-positive classification (e.g., a probability that a nucleotide-base call is a false positive variant), ii) a genotype-error classification (e.g., a probability of incorrectly identifying a genotype of a nucleotide-base call), and a iii) true-positive classification (e.g., a probability that a nucleotide-base call is a true positive variant). In some cases, the variant-call classifications accordingly represent variant-caller-intermediate-scoring metrics.

From the variant-call classifications, the base-caller-recalibration system can further modify or update (metrics for) a final nucleotide-base call for a genomic coordinate (e.g., a final nucleotide-base call that indicates a variant call or a non-variant call). For example, the base-caller-recalibration system utilizes the variant-call classifications to update data fields corresponding to call quality, genotype, and genotype quality within a digital call file (e.g., a variant call format file or other base-call-output file) that indicates or represents a nucleotide-base call. Indeed, as mentioned above, in some embodiments, the base-caller-recalibration system utilizes a call-generation model to generate or determine a final nucleotide-base call from the sequencing metrics for the genomic coordinate.

Additionally, the base-caller-recalibration system can utilize the variant-call classifications to update the nucleotide-base call for improved accuracy. In certain implementations, the base-caller-recalibration system generates the variant-call classifications utilizing the call-recalibration-machine-learning model while also utilizing the call-generation model to generate the nucleotide-base call based on the variant-call classifications. Indeed, in some embodiments, the base-caller-recalibration system utilizes (i) the call-generation model to generate an initial nucleotide-base call and (ii) the call-recalibration-machine-learning model to modify data fields corresponding to a variant call file for the nucleotide-base call. In some cases, the base-caller-recalibration system further edits the nucleotide-base call based on one or more of the data fields and generates a variant call file with the edited nucleotide-base call. By contrast, in some cases, the base-caller-recalibration system determines a final nucleotide-base call for a genomic coordinate based on both sequencing metrics for a call-generation model and variant-call classifications from the call-recalibration-machine-learning model—without an initial nucleotide-base call from the call-generation model. For example, in some embodiments, the call-generation model may output a final variant call that accounts for the variant-call classifications (without generating an initial variant call that is updated. By contrast, in certain cases, the call-generation model may initially determine a confidence or quality corresponding to a potential variant call fails to satisfy a threshold for including in a variant call file but (after accounting for variant-call classifications that updates a base-call-quality metric) determine to include a variant call in the variant call file. As a result of implementing the call-recalibration-machine-learning model and the call-generation model in this way, the base-caller-recalibration system recovers false negative calls and/or removes false positive calls initially made by the call-generation model.

In one or more embodiments, the base-caller-recalibration system further determines contribution measures associated with one or more of the sequencing metrics. In particular, the base-caller-recalibration system determines measures of impact or influence that each sequencing metric or a subset of sequencing metrics has on a final nucleotide-base call. For example, some metrics may be more heavily weighted than others in determining a call at one genomic coordinate versus another. Indeed, due to the accessibility and interpretability of the call-generation model and the call-recalibration-machine-learning model, the base-caller-recalibration system can access internal sequencing metrics used to generate a nucleotide-base call and can determine their respective contribution measures in ultimately determining which metrics are causing or driving the recalibration of the nucleotide-base calls (e.g., variant calls). In some cases, the base-caller-recalibration system further generates and provides a visualization of the contribution measures for display on a client device.

As suggested above, the base-caller-recalibration system provides several advantages, benefits, and/or improvements over existing sequencing systems, including variant callers and other sequencing-data-analysis software. For instance, the base-caller-recalibration system introduces a first-of-its-kind machine-learning model—the call-recalibration-machine-learning model—that is uniquely trained to perform a new application. Unlike conventional variant callers that generate nucleotide-base calls exclusively from raw extracted metrics, the base-caller-recalibration system utilizes a unique call-recalibration-machine-learning model that generates specific variant-call classifications from external and internal sequencing metrics. Indeed, in some cases, the base-caller-recalibration system utilizes the call-recalibration-machine-learning model to update a nucleotide-base call generated by a call-generation model from the same (or a subset of the same) metrics used by the call-recalibration-machine-learning model to generate the variant-call classifications.

In addition to introducing a first-of-its-kind machine-learning model, compared to existing sequencing systems, the genomic-classification system improves the accuracy of nucleotide-base calls. Indeed, while some existing sequencing systems generate nucleotide-base calls with some degree of accuracy, these systems nevertheless identify excessive numbers of false positive variant calls (e.g., by identifying a variant where none exists in a reference sequence) and/or filter out excessive numbers of false negative variant calls (e.g., by identifying a genomic position as non-variant when, in fact, the position has a variant). The base-caller-recalibration system improves upon the accuracies of existing systems by removing large numbers of false positives and recovering large numbers of false negatives utilizing the call-recalibration-machine-learning model. By editing an initial nucleotide-base call or generating a final nucleotide-base call based on variant-call classifications from the call-recalibration-machine-learning model, the base-caller-recalibration system can use unique machine-learning outputs to recalibrate base calls with better accuracy than existing variant callers or machine-learning models for variant calling. For instance, the base-caller-recalibration system utilizes the call-recalibration-machine-learning model to generate variant-call classifications from both internal (e.g., proprietary and model-specific) and external sequencing metrics, which results in recovering variant-nucleotide-base calls that were previously filtered out and/or removing non-variant-nucleotide-base calls that were previously not filtered out.

Contributing at least in part to the improved accuracy, the base-caller-recalibration system exhibits improved flexibility over existing sequencing systems. For example, as mentioned above, existing sequencing systems sometimes utilize variant callers that rely exclusively on internal sequencing metrics for particular base calls to generate a nucleotide-base call—without re-engineering or modifying such internal sequencing metrics or analyzing externally sourced sequencing metrics relevant to the genomic coordinates of corresponding nucleotide-base calls. By contrast, in some embodiments, the base-caller-recalibration system generates and manipulates both external and internal sequencing metrics. Indeed, in some cases, the base-caller-recalibration system determines call-model-generated sequencing metrics from variant-caller components and mapping-and-alignment components of a call-generation model by combining Bayesian probabilistic models with machine learning techniques in an efficient manner. In addition, the base-caller-recalibration system utilizes a call-recalibration-machinelearning model to generate an updated nucleotide-base call (e.g., from variant-call classifications) from one or more sequencing metrics.

In addition to improved accuracy and flexibility, in certain embodiments, the base-caller-recalibration system improves efficiency and speed. As noted above, some existing sequencing systems utilize computationally expensive, slow neural network architectures (e.g., deep learning architectures such as convolutional neural networks) that require many hours (e.g., 5-8 hours with multiple processors executing on a server) and large amounts of computational resources to even implement and generate a file with variant calls from a sequencing run. Such deep learning architectures can further require several days (or weeks) to train. Conversely, the base-caller-recalibration system utilizes comparatively lightweight, fast architectures for both the call-generation model and the call-recalibration-machine-learning model. Indeed, contrasting with the many hours across multiple processors required by prior systems, the base-caller-recalibration system, in many cases, requires under 30 minutes (for both the call-generation model and the call-recalibration-machine-learning model together) of runtime on a single field-programmable-gate array or a single processor to generate nucleotide-base calls for a sample nucleotide sequence. Thus, the base-caller-recalibration system is far faster and less computationally expensive than many deep learning approaches to variant calling. Not only are the models of the base-caller-recalibration system faster and less computationally expensive to implement, but the models of the base-caller-recalibration system are also much faster and less computationally expensive to train than many existing deep-learning-based systems.

As part of the improved speed and efficiency, in some embodiments, the base-caller-recalibration system recalibrates nucleotide-base calls on a call-by-call basis as each call is processed by the call-generation model. Indeed, the base-caller-recalibration system can generate variant-call classifications for recalibrating a nucleotide-base call (e.g., utilize the call-recalibration-machine-learning model) while also generating the nucleotide-base call from the variant-call classifications along with one or more sequencing metrics. In some embodiments, the base-caller-recalibration system utilizes the call-generation model in parallel with the call-recalibration-machine-learning model to contemporaneously generate an initial nucleotide-base call and variant-call classifications for modifying or recalibrating the initial nucleotide-base call.

As a further advantage over existing sequencing systems, in certain implementations, the base-caller-recalibration system can identify or facilitate changes to individual metrics that affect the accuracy of nucleotide-base calls. While the neural network architectures of many conventional systems render any interpretation of internal model data impossible with latent features, the base-caller-recalibration system utilizes model architectures that facilitate interpretation of the effect of individual sequencing metrics. More specifically, in some cases, the base-caller-recalibration system utilizes a call-generation model and a call-recalibration-machine-learning model that enable extraction and analysis of individual sequencing metrics used throughout the process of generating a nucleotide-base call. Indeed, the base-caller-recalibration system can determine respective contribution measures for sequencing metrics involved in determining a nucleotide-base call at a particular genomic coordinate.

As suggested by the foregoing discussion, this disclosure utilizes a variety of terms to describe features and benefits of the base-caller-recalibration system. Additional detail is hereafter provided regarding the meaning of these terms as used in this disclosure. As used in this disclosure, for instance, the term "sample nucleotide sequence" or "sample sequence" refers to a sequence of nucleotides isolated or extracted from a sample organism (or a copy of such an isolated or extracted sequence). In particular, a sample nucleotide sequence includes a segment of a nucleic-acid polymer that is isolated or extracted from a sample organism and composed of nitrogenous heterocyclic bases. For example, a sample nucleotide sequence can include a segment of deoxyribonucleic acid (DNA), ribonucleic acid (RNA), or other polymeric forms of nucleic acids or chimeric or hybrid forms of nucleic acids noted below. More specifically, in some cases, the sample nucleotide sequence is found in a sample prepared or isolated by a kit and received by a sequencing device.

As further used herein, the term "nucleotide-base call" (or sometimes simply "call") refers to a determination or prediction of a particular nucleotide base (or nucleotide-base pair) for a genomic coordinate of a sample genome or for an oligonucleotide during a sequencing cycle. In particular, a nucleotide-base call can indicate (i) a determination or prediction of the type of nucleotide base that has been incorporated within an oligonucleotide on a nucleotide-sample slide (e.g., read-based nucleotide-base calls) or (ii) a determination or prediction of the type of nucleotide base that is present at a genomic coordinate or region within a sample genome, including a variant call or a non-variant call in a digital output file. In some cases, for a nucleotide read, a nucleotide-base call includes a determination or a prediction of a nucleotide base based on intensity values resulting from fluorescent-tagged nucleotides added to an oligonucleotide of a nucleotide-sample slide (e.g., in a well of a flow cell). Alternatively, a nucleotide-base call includes a determination or a prediction of a nucleotide base to chromatogram peaks or electrical current changes resulting from nucleotides passing through a nanopore of a nucleotide-sample slide. By contrast, a nucleotide-base call can also include an initial or final prediction of a nucleotide base at a genomic coordinate of a sample genome for a variant call file or other base-call-output file-based on nucleotide reads corresponding to the genomic coordinate. Accordingly, a nucleotide-base call can include a base call corresponding to a genomic coordinate and a reference genome, such as an indication of a variant or a non-variant at a particular location corresponding to the reference genome. Indeed, a nucleotide-base call can refer to a variant call, including but not limited to, a single nucleotide polymorphism (SNP), an insertion or a deletion (indel), or base call that is part of a structural variant. By using nucleotide-base call, a sequencing system determines a sequence of a nucleic-acid polymer. For example, a single nucleotide-base call can comprise an adenine call, a cytosine call, a guanine call, or a thymine call for DNA (abbreviated as A, C, G, T) or a uracil call (instead of a thymine call) for RNA (abbreviated as U).

Relatedly, as used herein, the term "nucleotide read" refers to an inferred sequence of one or more nucleotide bases (or nucleotide-base pairs) from all or part of a sample nucleotide sequence. In particular, a nucleotide read includes a determined or predicted sequence of nucleotide-base calls for a nucleotide fragment (or group of monoclonal nucleotide fragments) from a sequencing library corresponding to a genome sample. For example, the base-caller-recalibration system determines a nucleotide read by generating nucleotide-base calls for nucleotide bases passed through a nanopore of a nucleotide-sample slide, determined via fluorescent tagging, or determined from a well in a flow cell.

As noted above, in some embodiments, the base-caller-recalibration system determines sequencing metrics for nucleotide-base calls of nucleotide reads. As used herein, the term "sequencing metric" refers to a quantitative measurement or score indicating a degree to which an individual nucleotide-base call (or a sequence of nucleotide-base calls) aligns, compares, or quantifies with respect to a genomic coordinate or genomic region of a reference genome, with respect to nucleotide-base calls from nucleotide reads, or with respect to external genomic sequencing or genomic structure. For instance, a sequencing metric includes a quantitative measurement or score indicating a degree to which (i) individual nucleotide-base calls align, map, or cover a genomic coordinate or reference base of a reference genome; (ii) nucleotide-base calls compare to reference or alternative nucleotide reads in terms of mapping, mismatch, base-call quality, or other raw sequencing metrics; or (iii) genomic coordinates or regions corresponding to nucleotide-base calls demonstrate mappability, repetitive base-call content, DNA structure, or other generalized metrics.

In some embodiments, the base-caller-recalibration system determines various types of sequencing metrics from different sources, such as read-based sequencing metrics, externally sourced sequencing metrics, and call-model-generated sequencing metrics. As used herein, the term "read-based sequencing metrics" refers to sequencing metrics derived from nucleotide reads of a sample nucleotide sequence. For example, read-based sequencing metrics include sequencing metrics determined by applying statistical tests to detect differences between a reference sequence and nucleotide reads. For example, read-based sequencing metrics can include a comparative-mapping-quality-distribution metric that indicates a comparison between mapping qualities or a comparative-mismatch-count metric that indicates a comparison between mismatch counts.

By contrast, "externally sourced sequencing metrics" refer to sequencing metrics identified or obtained from one or more external databases. For example, externally sourced sequencing metrics include metrics relating to mappability of nucleotides, replication timing, or DNA structure that are available outside of the base-caller-recalibration system.

Further, "call-model-generated sequencing metrics" refer to internal, model-specific sequencing metrics generated or extracted by a call-generation model. For example, call-model-generated sequencing metrics include variant-calling sequencing metrics extracted or determined via variant-caller components of a call-generation model and mapping-and-alignment sequencing metrics extracted or determined via mapping-and-alignment components of a call-generation model. As indicated above, call-model-generated sequencing metrics can include alignment metrics that quantify a degree to which sample nucleic-acid sequences align with genomic coordinates of an example nucleic-acid sequence, such as deletion-size metrics or mapping-quality metrics. Further, call-model-generated sequencing metrics can include depth metrics that quantify the depth of nucleotide base calls for sample nucleic-acid sequences at genomic coordinates of an example nucleic-acid sequence, such as forward-reverse-depth metrics or normalized-depth metrics. Call-model-generated sequencing metrics can also include call-quality metrics that quantify a quality or accuracy of nucleotide base calls, such as nucleotide base-call-quality metrics, callability metrics, or somatic-quality metrics.

As used herein, the term "base-call-quality metric" refers to a specific score or other measurement indicating an accuracy of a nucleotide-base call. In particular, a base-call-quality metric comprises a value indicating a likelihood that one or more predicted nucleotide-base calls for a genomic coordinate contain errors. For example, in certain implementations, a base-call-quality metric can comprise a Q score (e.g., a Phred quality score) predicting the error probability of any given nucleotide-base call. To illustrate, a quality score (or Q score) may indicate that a probability of an incorrect nucleobase call at a genomic coordinate is equal to 1 in 100 for a Q20 score, 1 in 1,000 for a Q30 score, 1 in 10,000 for a Q40 score, etc.

Relatedly, as used herein, the term "re-engineered sequencing metrics" refers to sequencing metrics that have been updated, modified, augmented, refined, or re-engineered to measure or compare nucleotide-base calls (e.g., nucleotide-base calls for reads or variant calls) with respect to other nucleotide-base calls, a standard or reference, or for targeted for a particular objective or task. For example, re-engineered sequencing metrics can include modifications to, or combinations of, raw sequencing metrics. In some embodiments, for instance, the base-caller-recalibration system generates one or more of the read-based sequencing metrics, the externally sourced sequencing metrics, and/or the call-model-generated sequencing metrics as re-engineered sequencing metrics. In some cases, re-engineered sequencing metrics refer to sequencing metrics that are generated by the base-caller-recalibration system and are therefore proprietary or internal to the base-caller-recalibration system and not available to third-party systems. Example re-engineered sequencing metrics include a comparative-mapping-quality-distribution metric indicating a comparison between mapping quality distributions associated with a reference sequence and alternatives supporting nucleotide reads or a comparative-base-quality metric indicating comparisons between base qualities of a reference sequence and alternative supporting nucleotide reads.

As further used herein, the term "genomic coordinate" refers to a particular location or position of a nucleotide base within a genome (e.g., an organism's genome or a reference genome). In some cases, a genomic coordinate includes an identifier for a particular chromosome of a genome and an identifier for a position of a nucleotide base within the particular chromosome. For instance, a genomic coordinate or coordinates may include a number, name, or other identifier for a chromosome (e.g., chr1 or chrX) and a particular position or positions, such as numbered positions following the identifier for a chromosome (e.g., chr1:1234570 or chr1:1234570-1234870). Further, in certain implementations, a genomic coordinate refers to a source of a reference genome (e.g., mt for a mitochondrial DNA reference genome or SARS-CoV-2 for a reference genome for the SARS-CoV-2 virus) and a position of a nucleotide base within the source for the reference genome (e.g., mt:16568 or SARS-CoV-2:29001). By contrast, in certain cases, a genomic coordinate refers to a position of a nucleotide base within a reference genome without reference to a chromosome or source (e.g., 29727).

As noted above, a genomic coordinate includes a position within a reference genome. Such a position may be within a particular reference genome. As used herein, the term "reference genome" refers to a digital nucleic-acid sequence assembled as a representative example (or representative examples) of genes and other genetic sequences of an organism. Regardless of the sequence length, in some cases, a reference genome represents an example set of genes or a set of nucleic-acid sequences in a digital nucleic-acid sequenced determined by scientists as representative of an organism of a particular species. For example, a linear human reference genome may be GRCh38 or other versions of reference genomes from the Genome Reference Consortium. As a further example, a reference genome may include a reference graph genome that includes both a linear reference genome and paths representing nucleic-acid sequences from ancestral haplotypes, such as Illumina DRAGEN Graph Reference Genome hg19.

As suggested above, the base-caller-recalibration system can utilize a machine learning model to modify sequencing metrics and update a nucleotide-base call. As used herein, the term "machine learning model" refers to a computer algorithm or a collection of computer algorithms that automatically improve for a particular task through experience based on use of data. For example, a machine learning model can utilize one or more learning techniques to improve in accuracy and/or effectiveness. Example machine learning models include various types of decision trees, support vector machines, Bayesian networks, or neural networks. In some cases, the call-recalibration-machine-learning model is a series of gradient boosted decision trees (e.g., XGBoost algorithm), while in other cases the call-recalibration-machine-learning model is a random forest model, a multilayer perceptron, a linear regression, a support vector machine, a deep tabular learning architecture, a deep learning transformer (e.g., self-attention-based-tabular transformer), or a logistic regression.

In some cases, the base-caller-recalibration system utilizes a call-recalibration-machine-learning model to modify or update a nucleotide-base call based on sequencing metrics. As used herein, the term "call-recalibration-machine-learning model" refers to a machine learning model that generates variant-call classifications. For example, in some cases, the call-recalibration-machine-learning model is trained to generate variant-call classifications indicating various probabilities or predictions for variant calls based on the sequencing metrics. Accordingly, in some cases, a call-recalibration-machine-learning model a variant-call-recalibration-machine-learning model. In certain embodiments, a call-recalibration-machine-learning model includes multiple sub-models or operates in tandem with another call-recalibration-machine-learning model. For instance, a first call-recalibration-machine-learning model (e.g., an ensemble of gradient boosted trees) generates a first set of variant-call classifications and a second call-recalibration-machine-learning model (e.g., a random forest) generates a second set of variant-call classifications.

Relatedly, the term "variant-call classification" refers to a predicted classification from a call-recalibration-machine-learning model that indicates a probability, score, or other quantitative measurement associated with some aspect of a nucleotide-base call based on one or more sequencing metrics. In some cases, a variant-call classification includes a predicted probability that a genotype for a nucleotide-base call is accurate. For example, in some embodiments, the call-recalibration-machine-learning model generates one or more of the following variant-call classifications: i) a false-positive classification indicating a probability that a nucleotide-base call is a false positive, ii) a genotype-error classification indicating a probability that a genotype (e.g., an indication of a heterozygous or homozygous genotype for a variant call at a particular location) is incorrect, and/or iii) a true-positive classification indicating a probability that a nucleotide-base call is a true positive. In some cases, the variant-call classifications accordingly represent variant-caller-intermediate-scoring metrics.

As mentioned, in some embodiments, the call-recalibration-machine-learning model can be a neural network. The term the term "neural network" refers to a machine learning model that can be trained and/or tuned based on inputs to determine classifications or approximate unknown functions. For example, a neural network includes a model of interconnected artificial neurons (e.g., organized in layers) that communicate and learn to approximate complex functions and generate outputs (e.g., generated digital images) based on a plurality of inputs provided to the neural network. In some cases, a neural network refers to an algorithm (or set of algorithms) that implements deep learning techniques to model high-level abstractions in data. For example, a neural network can include a convolutional neural network, a recurrent neural network (e.g., an LSTM), a graph neural network, a self-attention transformer neural network, or a generative adversarial neural network.

As noted above, the base-caller-recalibration system can generate variant-call classifications that indicate or reflect a likelihood of identifying a variant at a genomic coordinate. As used herein, the term "variant" refers to a nucleotide base or multiple nucleotide bases that do not align with, differs from, or varies from a corresponding nucleotide base (or nucleotide bases) in a reference sequence or a reference genome. For example, a variant includes a SNP, an indel, or a structural variant that indicates nucleotide bases in a sample nucleotide sequence that differ from nucleotide bases in corresponding genomic coordinates of a reference sequence. Along these lines, a "variant-nucleotide-base call" refers to a nucleotide-base call comprising a variant at a particular genomic coordinate. Conversely, a "non-variant-nucleotide-base call" refers to a nucleotide-base call comprising a non-variant at a genomic coordinate.

As mentioned, in some embodiments, the base-caller-recalibration system modifies data fields corresponding to a variant call file. As used herein, the term "variant call file" refers to a digital file that indicates or represents one or more nucleotide-base calls (e.g., variant calls) compared to a reference genome along with other information pertaining to the nucleotide-base calls (e.g., variant calls). For example, a variant call format (VCF) file refers to a text file format that contains information about variants at specific genomic coordinates, including meta-information lines, a header line, and data lines where each data line contains information about a single nucleotide-base call (e.g., a single variant). As described further below, the base-caller-recalibration system can generate different versions of variant call files, including a pre-filter variant call file comprising variant-nucleotide-base calls that either pass or fail a quality filter for base-call-quality metrics or a post-filter variant call file comprising variant-nucleotide-base calls that pass the quality filter but excludes variant-nucleotide-base calls that fail the quality filter. In some embodiments, the base-caller-recalibration system modifies data fields corresponding to metrics of a nucleotide-base call associated with a variant call file, such as fields for call quality, genotype, and genotype quality. As used herein, the term "call quality" when used with respect to a data field in a variant call file refers to a measure or an indication of a likelihood or a probability that a variant exists at a given location. Accordingly, a call quality field (or QUAL field) corresponding to a VCF file may include a base-call-quality metric, such as a Phred-scaled quality or Q score, representing a probability that a genomic coordinate of a sample genome includes a variant. Similarly, a "genotype quality" when used with respect to a field refers to a likelihood or a probability that a particular predicted geno-type for a nucleotide-base call is correct.

As noted, in some embodiments, the base-caller-recali-bration system utilizes a call-generation model to generate a nucleotide-base call for a genomic coordinate. As used herein, the term "call-generation model" refers to a proba-bilistic model that generates sequencing data from nucleo-tide reads of a sample nucleotide sequence, including nucleotide-base calls and associated metrics. Accordingly, in some cases, a call-generation model may be a variant-call-generation model. For example, in some cases, a call-generation model refers to a Bayesian probability model that generates variant calls based on nucleotide reads of a sample nucleotide sequence. Such a model can process or analyze sequencing metrics corresponding to read pileups (e.g., multiple nucleotide reads corresponding to a single genomic coordinate), including mapping quality, base quality, and various hypotheses including foreign reads, missing reads, joint detection, and more. A call-generation model may likewise include multiple components, including, but not limited to, different software applications or components for mapping and aligning, sorting, duplicate marking, comput-ing read pileup depths, and variant calling. In some cases, the call-generation model refers to the ILLUMINA DRA-GEN model for variant calling functions and mapping and alignment functions.

As mentioned above, in certain described embodiments, the base-caller-recalibration system generates or determines contribution measures associated with individual sequenc-ing metrics. As used herein, the term "contribution measure" refers to a measure of effect, influence, or impact that a sequencing metric has on a given recalibration of fields for a base-call-output file (e.g., a variant call file), a given nucleotide-base call in a base-call-output file, or (in particu-lar) a given variant call. For example, a contribution mea-sure indicates how much of a role one sequencing metric plays in determining a nucleotide-base call over a different nucleotide-base call (and compared to other sequencing metrics).

The following paragraphs describe the base-caller-recali-bration system with respect to illustrative figures that portray example embodiments and implementations. For example, FIG. 1 illustrates a schematic diagram of a system environ-ment (or "environment") 100 in which a base-caller-recali-bration system 106 operates in accordance with one or more embodiments. As illustrated, the environment 100 includes one or more server device(s) 102 connected to a client device 108 and a sequencing device 114 via a network 112. While FIG. 1 shows an embodiment of the base-caller-recalibration system 106, this disclosure describes alterna-tive embodiments and configurations below.

As shown in FIG. 1, the server device(s) 102, the client device 108, and the sequencing device 114 can communicate with each other via the network 112. The network 112 comprises any suitable network over which computing devices can communicate. Example networks are discussed in additional detail below with respect to FIG. 10.

As indicated by FIG. 1, the sequencing device 114 com-prises a device for sequencing a nucleic-acid polymer. In some embodiments, the sequencing device 114 analyzes nucleic-acid segments or oligonucleotides extracted from samples to generate nucleotide reads or other data utilizing computer implemented methods and systems (described herein) either directly or indirectly on the sequencing device 114. More particularly, the sequencing device 114 receives and analyzes, within nucleotide-sample slides (e.g., flow cells), nucleic-acid sequences extracted from samples. In one or more embodiments, the sequencing device 114 uti-lizes SBS to sequence nucleic-acid polymers into nucleotide reads. In addition or in the alternative to communicating across the network 112, in some embodiments, the sequenc-ing device 114 bypasses the network 112 and communicates directly with the client device 108.

As further indicated by FIG. 1, the server device(s) 102 may generate, receive, analyze, store, and transmit digital data, such as data for determining nucleotide-base calls or sequencing nucleic-acid polymers. As shown in FIG. 1, the sequencing device 114 may send (and the server device(s) 102 may receive) call data from the sequencing device 114. The server device(s) 102 may also communicate with the client device 108. In particular, the server device(s) 102 can send data to the client device 108, including a variant call file or other information indicating nucleotide-base calls, sequencing metrics, error data, or other metrics associated with a nucleotide-base call, such as a call quality, a geno-type, and a genotype quality.

In some embodiments, the server device(s) 102 comprise a distributed collection of servers where the server device(s) 102 include a number of server devices distributed across the network 112 and located in the same or different physical locations. Further, the server device(s) 102 can comprise a content server, an application server, a communication server, a web-hosting server, or another type of server.

As further shown in FIG. 1, the server device(s) 102 can include a sequencing system 104. Generally, the sequencing system 104 analyzes call data, such as sequencing metrics received from the sequencing device 114, to determine nucleotide base sequences for nucleic-acid polymers. For example, the sequencing system 104 can receive raw data from the sequencing device 114 and determine a nucleotide base sequence for a nucleic-acid segment. In some embodi-ments, the sequencing system 104 determines the sequences of nucleotide bases in DNA and/or RNA segments or oligonucleotides. In addition to processing and determining sequences for nucleic-acid polymers, the sequencing system 104 also generates a variant call file indicating one or more nucleotide-base calls for one or more genomic coordinates.

As just mentioned, and as illustrated in FIG. 1, the base-caller-recalibration system 106 analyzes call data, such as sequencing metrics from the sequencing device 114, to determine nucleotide base calls for sample nucleic-acid sequences. The base-caller-recalibration system 106 includes a call-generation model and a call-recalibration-machine-learning model. In some embodiments, the base-caller-recalibration system 106 determines sequencing met-rics for sample nucleotide sequences. Based on data derived or prepared from the sequencing metrics, the base-caller-recalibration system 106 trains and applies a call-generation model to determine nucleotide-base calls for the sample sequence corresponding to genomic coordinates. The base-caller-recalibration system 106 further utilizes a call-recali-bration-machine-learning model to generate sets of variant-call classifications to update or modify the nucleotide-base calls based on various probabilities, such as a false-positive probability, a genotype-error probability, and/or a true-positive probability. Based on such data, for example, the base-caller-recalibration system 106 can update data fields corresponding to a variant call file to update a nucleotide-base call for improved accuracy.

As further illustrated and indicated in FIG. 1, the client device 108 can generate, store, receive, and send digital data. In particular, the client device 108 can receive sequenc-ing metrics from the sequencing device 114. Furthermore, the client device 108 may communicate with the server device(s) 102 to receive a variant call file comprising nucleotide base calls and/or other metrics, such as a call-quality, a genotype indication, and a genotype quality. The client device 108 can accordingly present or display information pertaining to the nucleotide-base call within a graphical user interface to a user associated with the client device 108. For example, the client device 108 can present a contribution-measure interface that includes a visualization or a depiction of various contribution measures associated with, or attributed to, individual sequencing metrics with respect to a particular nucleotide-base call.

The client device 108 illustrated in FIG. 1 may comprise various types of client devices. For example, in some embodiments, the client device 108 includes non-mobile devices, such as desktop computers or servers, or other types of client devices. In yet other embodiments, the client device 108 includes mobile devices, such as laptops, tablets, mobile telephones, or smartphones. Additional details regarding the client device 108 are discussed below with respect to FIG. 10.

As further illustrated in FIG. 1, the client device 108 includes a sequencing application 110. The sequencing application 110 may be a web application or a native application stored and executed on the client device 108 (e.g., a mobile application, desktop application). The sequencing application 110 can include instructions that (when executed) cause the client device 108 to receive data from the base-caller-recalibration system 106 and present, for display at the client device 108, data from a variant call file. Furthermore, the sequencing application 110 can instruct the client device 108 to display a visualization of contribution measures for sequencing metrics of a nucleotide-base call.

As further illustrated in FIG. 1, the base-caller-recalibration system 106 may be located on the client device 108 as part of the sequencing application 110 or on the sequencing device 114. Accordingly, in some embodiments, the base-caller-recalibration system 106 is implemented by (e.g., located entirely or in part) on the client device 108. In yet other embodiments, the base-caller-recalibration system 106 is implemented by one or more other components of the environment 100, such as the sequencing device 114. In particular, the base-caller-recalibration system 106 can be implemented in a variety of different ways across the server device(s) 102, the network 112, the client device 108, and the sequencing device 114. For example, the base-caller-recalibration system 106 can be downloaded from the server device(s) 102 to the client device 108 and/or to the sequencing device 114 where all or part of the functionality of the base-caller-recalibration system 106 is performed at each respective device within the environment 100.

As further illustrated in FIG. 1, the environment 100 includes a database 116. The database 116 can store information such as variant call files, sample nucleotide sequences, nucleotide reads, nucleotide-base calls, and sequencing metrics. In some embodiments, the server device(s) 102, the client device 108, and/or the sequencing device 114 communicate with the database 116 (e.g., via the network 112) to store and/or access information, such as variant call files, sample nucleotide sequences, nucleotide reads, nucleotide-base calls, and sequencing metrics. In some cases, the database 116 also stores one or more models, such as a call-recalibration-machine-learning model and/or a call-generation model.

Though FIG. 1 illustrates the components of environment 100 communicating via the network 112, in certain implementations, the components of environment 100 can also communicate directly with each other, bypassing the network. For instance, and as previously mentioned, in some implementations, the client device 108 communicates directly with the sequencing device 114. Additionally, in some embodiments, the client device 108 communicates directly with the base-caller-recalibration system 106. Moreover, the base-caller-recalibration system 106 can access one or more databases housed on or accessed by the server device(s) 102 or elsewhere in the environment 100.

Figure 2:
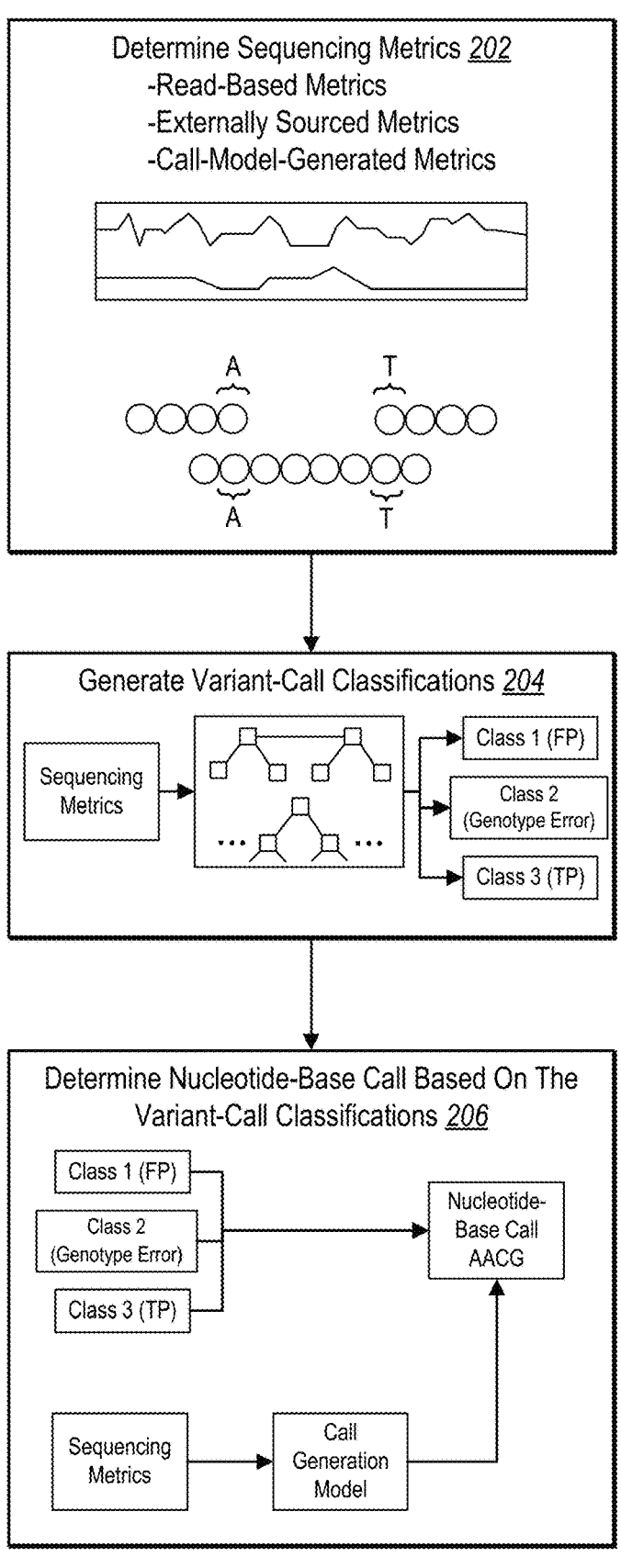
FIG. 2 illustrates an overview of generating a nucleotide-base call utilizing the base-caller-recalibration system in accordance with one or more embodiments.

As indicated above, the base-caller-recalibration system 106 can determine a nucleotide-base call based on one or more variant-call classifications. In particular, the base-caller-recalibration system 106 can determine variant-call classifications from sequencing metrics utilizing a call-recalibration-machine-learning model and can determine or update various metrics associated with a nucleotide-base call from the generated variant-call classifications. FIG. 2 illustrates an example sequence of acts the base-caller-recalibration system 106 performs to determine a nucleotide-base call based on variant-call classifications in accordance with one or more embodiments.

As illustrated in FIG. 2, the base-caller-recalibration system 106 performs an act 202 to determine sequencing metrics. In particular, the base-caller-recalibration system 106 determines sequencing metrics such as read-based sequencing metrics, externally sourced sequencing metrics, and call-model-generated sequencing metrics. For example, the base-caller-recalibration system 106 determines sequencing metrics that indicate various attributes or data in relation to various nucleotide-base calls of nucleotide reads from a sample nucleotide sequence. Additional detail regarding determining the various types of sequencing metrics is provided below with reference to FIGS. 3A-3C.

As further illustrated in FIG. 2, the base-caller-recalibration system 106 performs an act 204 to generate variant-call classifications. More specifically, the base-caller-recalibration system 106 generates (or updates or refines) variant-call classifications from sequencing metrics utilizing a call-recalibration-machine-learning model. To elaborate, the base-caller-recalibration system 106 utilizes the call-recalibration-machine-learning model to process or analyze one or more sequencing metrics and to generate a set of classifications (e.g., predicted probabilities associated with genotype). For instance, the base-caller-recalibration system 106 generates, utilizing the call-recalibration-machine-learning model, a set of variant-call classifications that indicate certain probabilities associated with a genotype of a corresponding nucleotide-base call based on the sequencing metrics.

In some embodiments, the base-caller-recalibration system 106 generates a false-positive classification utilizing the call-recalibration-machine-learning model (represented in FIG. 2 as "FP"). For example, the base-caller-recalibration system 106 generates a false-positive classification that indicates a probability that a nucleotide-base call (e.g., genotype call) is a false positive variant, or that the nucleotide-base call indicates a variant where no variant actually exists within a sample nucleotide sequence in relation to a reference nucleotide sequence. The base-caller-recalibration system 106 generates the false-positive classification from one or more sequencing metrics considered together by the call-recalibration-machine-learning model.

In certain implementations, the base-caller-recalibration system 106 also (or alternatively) generates a genotype-error classification (represented in FIG. 2 as "Genotype Error"). More specifically, the base-caller-recalibration system 106 determines, utilizing the call-recalibration-machine-learning model, a probability that a genotype associated with a nucleotide-base call is incorrect. For instance, the base-caller-recalibration system 106 determines a probability that a het/hom error exists for a nucleotide-base call, where the nucleotide-base call may indicate a heterozygous genotype for nucleotide bases at a genomic coordinate or region within a sample genome where the sample genome's nucleotide base(s) are actually homozygous at the corresponding genomic coordinate or region. Conversely, the base-caller-recalibration system 106 determines a probability of determining that a genotype for a nucleotide-base call is homozygous when the corresponding nucleotide base(s) are heterozygous.

In one or more embodiments, the base-caller-recalibration system 106 also (or alternatively) generates a true-positive classification (represented in FIG. 2 as "TP"). In particular, the base-caller-recalibration system 106 determines, utilizing the call-recalibration-machine-learning model, a probability that a nucleotide-base call (e.g., genotype call) is a true positive variant, or that a nucleotide-base call indicates a true variant within a sample nucleotide sequence where a variant does indeed exist within a reference nucleotide sequence at the corresponding genomic coordinate. Additional detail regarding generating variant-call classifications is provided below with reference to subsequent figures.

As further illustrated in FIG. 2, the base-caller-recalibration system 106 also performs an act 206 to determine a nucleotide-base call based on the variant-call classifications. More particularly, the base-caller-recalibration system 106 determines a nucleotide-base call for a sample nucleotide sequence at a genomic coordinate within a reference genome. To determine or generate the nucleotide-base call, in some embodiments the base-caller-recalibration system 106 determines initial nucleotide-base calls utilizing a call-generation model and edits or updates certain initial nucleotide-base calls based on the variant-call classifications generated by the call-recalibration-machine-learning model.

To elaborate, the base-caller-recalibration system 106 utilizes a call-generation model to process or analyze sequencing metrics (e.g., one or more of the same sequencing metrics used to generate the variant-call classifications in act 204) to determine a nucleotide-base call from the sequencing metrics. For example, the base-caller-recalibration system 106 applies a number of Bayesian probabilistic models or algorithms to derive various probabilities for different nucleotide bases, quality metrics, mapping metrics, joint metrics, and other data occurring within the sample nucleotide sequence to include within a variant call file. From the probabilistic models, the base-caller-recalibration system 106 determines a final nucleotide-base call (e.g., a call indicating a difference or sameness to a reference base from a reference genome) that indicates a predicted nucleotide base for the sample genome at a corresponding genomic coordinate.

As further illustrated in FIG. 2, in certain implementations, the base-caller-recalibration system 106 utilizes the initial variant-call classifications (e.g., as determined via the act 204) to generate, recalibrate, determine, modify, or augment the nucleotide-base call. To elaborate, the base-caller-recalibration system 106 utilizes probabilities associated with the three variant-call classifications to determine or update certain metrics associated with a nucleotide-base call. For example, the base-caller-recalibration system 106 modifies data fields corresponding to a variant call file for metrics, such as call quality, genotype, and genotype quality.

In some cases, the base-caller-recalibration system 106 extrapolates from the variant-call classifications to determine metrics corresponding to a variant call file, such as call quality, genotype, and genotype quality associated with the nucleotide-base call. Indeed, by utilizing the genotype-error classification, the base-caller-recalibration system 106 can remedy certain errors in or associated with an initial nucleotide-base call. For instance, if the base-caller-recalibration system 106 determines a high false-positive probability for a nucleotide-base call, then the base-caller-recalibration system 106 applies the call-recalibration-machine-learning model to function as a variant filter to modify (e.g., reduce) a call quality associated with the nucleotide-base call. As another example, the base-caller-recalibration system 106 utilizes the genotype-error probability to modify a genotype and/or a genotype quality of a nucleotide-base call in cases where systems would previously filter out or doubly penalize het/hom errors (e.g., where the system generates a nucleotide-base call that is incorrect which further results in missing a nucleotide-base call that is correct).

In certain embodiments, the base-caller-recalibration system 106 considers a single variant-call classification to modify a data field for a nucleotide-base call (e.g., a call quality, a genotype, or a genotype quality). In other embodiments, the base-caller-recalibration system 106 considers multiple variant-call classifications at once (e.g., in a weighted combination) to modify or update one or more data fields for call quality, genotype, and/or genotype quality. Additional detail regarding generating and modifying nucleotide-base calls is provided below with reference to subsequent figures.

In one or more implementations, the base-caller-recalibration system 106 generates the variant-call classifications (e.g., via the act 204) while or during the process of determining a nucleotide-base call. For example, the base-caller-recalibration system 106 simultaneously implements the call-recalibration-machine-learning model and the call-generation model to generate a nucleotide-base call and variant-call classifications for modifying the nucleotide-base call. The base-caller-recalibration system 106 further modifies data fields corresponding to a variant call file of the nucleotide-base call to generate a finalized nucleotide-base call (e.g., within a pre-filter or post-filter variant call file). Indeed, the base-caller-recalibration system 106 generates the finalized (e.g., recalibrated) nucleotide-base call from the variant-call classifications as well as sequencing metrics processed by the call-generation model (e.g., one or more of the same sequencing metrics used to generate the variant-call classifications). As described above, this simultaneous or parallel operation affords the base-caller-recalibration system 106 improved computational efficiency and increased speed by recalibrating nucleotide-base calls as they are initially generated (rather than performing one operation before the other).

In one or more implementations, the base-caller-recalibration system 106 determines a nucleotide-base call as part of a SNP, a deletion, an insertion, or a structural variation. For example, the base-caller-recalibration system 106 determines a nucleotide-base call represent an SNP at a genomic coordinate (e.g., chr1:151863125) by identifying a G in the sample nucleotide sequence where an A exists in the reference sequence. As another example, the base-caller-recalibration system 106 determines nucleotide-base calls surrounding one or more genomic coordinates (e.g., chr1: 49263256) indicate a deletion by identifying a single G in the sample nucleotide sequence where GTAAC exists in the reference sequence.

As a further example, the base-caller-recalibration system 106 determines a sequence of nucleotide-base calls represent an insertion at a genomic coordinate (e.g., chr1:7602080) by identifying a sequence of TTTCC in the sample nucleotide sequence where a T exists in the reference sequence. Indeed, in some cases, an insertion includes a sequence of nucleotide-base calls that replace a single reference base at a genomic coordinate of a reference sequence.

Figures 3A, 3B:
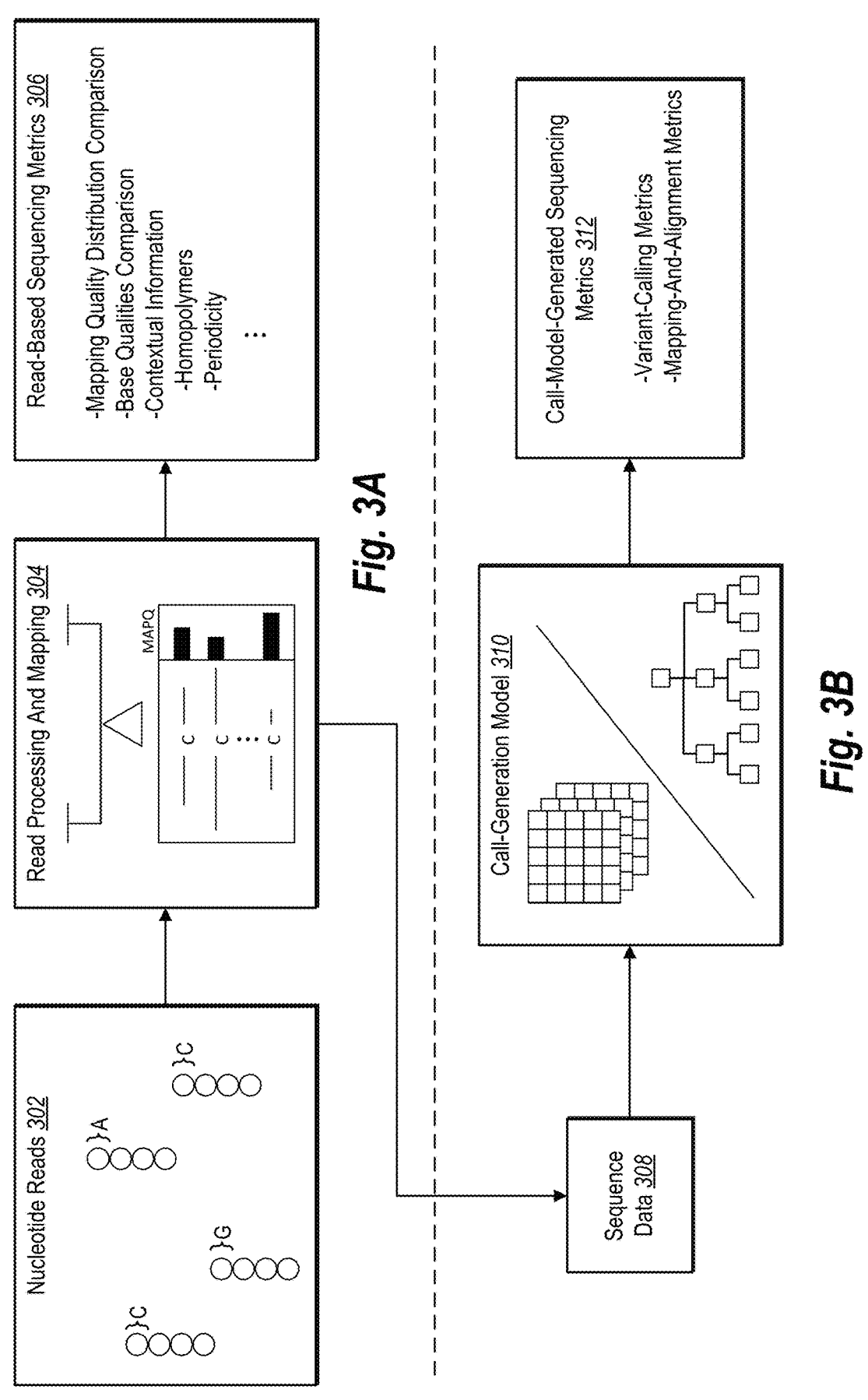
FIGS. 3A-3C illustrate generating or determining sequencing metrics in accordance with one or more embodiments.
Figure 3C:
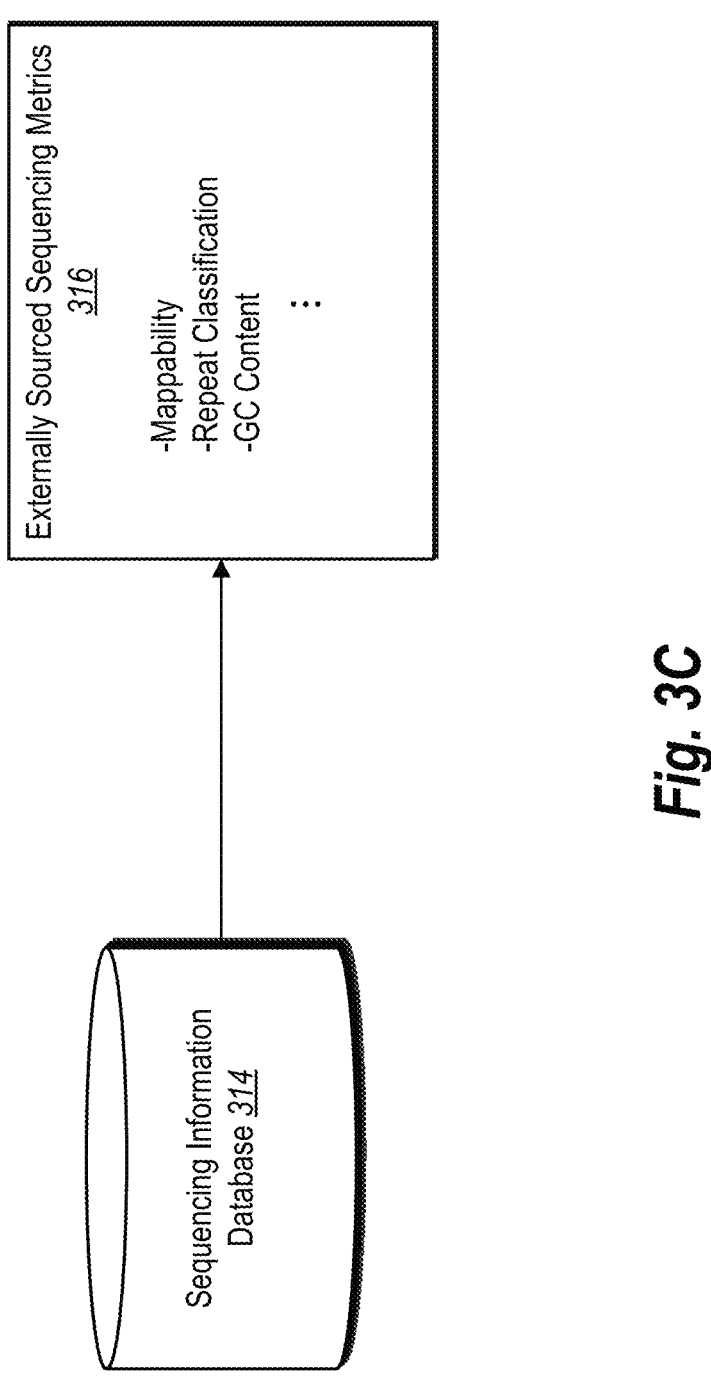

As mentioned above, in certain described embodiments, the base-caller-recalibration system 106 determines or extracts sequencing metrics for nucleotide-base calls. In particular, the base-caller-recalibration system 106 determines sequencing metrics such as read-based sequencing metrics, externally sourced sequencing metrics, and call-model-generated sequencing metrics from calls corresponding to nucleotide reads from a sample nucleotide sequence. FIGS. 3A-3C illustrate determining sequencing metrics in accordance with one or more embodiments. Specifically, FIG. 3A illustrates determining read-based sequencing metrics while FIG. 3B illustrates determining call-model-generated sequencing metrics, and FIG. 3C illustrates determining externally sourced sequencing metrics.

As illustrated in FIG. 3A, the base-caller-recalibration system 106 accesses, retrieves, obtains, determines, or generates nucleotide reads 302. In particular, the base-caller-recalibration system 106 determines the nucleotide reads 302 utilizing the sequencing device 114 comprising nucleotide-base calls for regions from a sample nucleotide sequence (e.g., sample genome). For example, the base-caller-recalibration system 106 generates a plurality of nucleotide reads 302 utilizing sequencing-by-synthesis (SBS) techniques and/or Sanger sequencing techniques to determine nucleotide-base calls for oligonucleotide clusters from wells in a flow cell and/or via fluorescent tagging. More specifically, the base-caller-recalibration system 106 utilizes cluster generation and SBS chemistry to sequence millions or billions of clusters in a flow cell. During SBS chemistry, for each cluster, the base-caller-recalibration system 106 stores nucleotide-base calls from the nucleotide reads 302 for every cycle of sequencing via real-time analysis (RTA) software.

As further illustrated in FIG. 3A, in some embodiments, the base-caller-recalibration system 106 performs read processing and mapping 304. For example, the base-caller-recalibration system 106 utilizes RTA software to store base-call data in the form of individual base-call data files (or BCLs). In some cases, the base-caller-recalibration system 106 further converts the BCL files into sequence data 308 (e.g., via BCL to FASTQ conversion), as illustrated in FIG. 3B. As shown in FIG. 3A, the base-caller-recalibration system 106 generates multiple-read coverage (e.g., read pileups) that include multiple nucleotide reads 302 or nucleotide-base calls corresponding to a single genomic coordinate.

In particular, in certain embodiments, the base-caller-recalibration system 106 aligns nucleotide reads with a reference genome or receives information pertaining to the read alignment. Specifically, the base-caller-recalibration system 106 determines which nucleotide base(s) of a given read align with which genomic coordinate of a reference sequence (or receives information indicating alignment). Different reads have different lengths and include different nucleotide bases. Accordingly, in some cases, the base-caller-recalibration system 106 analyzes each nucleotide of each read to determine (or receives information indicating) where the read "fits" in relation to a reference sequence—e.g., where the bases within the read align with bases in the reference. In some cases, the base-caller-recalibration system 106 aligns many reads at a single genomic coordinate, thus resulting a read pileup.

In certain embodiments, the base-caller-recalibration system 106 performs additional statistical tests to determine or detect differences between metrics associated with a reference nucleotide sequence and metrics associated with alternative supporting nucleotide reads. Through these statistical tests, the base-caller-recalibration system 106 re-engineers raw sequencing metrics to determine read-based sequencing metrics 306. In some cases, the base-caller-recalibration system 106 determines or extracts raw sequencing metrics that include one or more of (i) alignment metrics for quantifying alignment of sample nucleotide sequences with genomic coordinates of an example nucleotide sequence (e.g., a reference genome or a nucleotide sequence from an ancestral haplotype), (ii) depth metrics for quantifying depth of nucleobase calls for sample nucleotide sequences at genomic coordinates of the example nucleotide sequence, or (iii) call-quality metrics for quantifying quality of nucleobase calls for sample nucleotide sequences at genomic coordinates of the example nucleotide sequence. For instance, the base-caller-recalibration system 106 determines mapping-quality metrics (e.g., the MAPQ metrics indicated in FIG. 3A), soft-clipping metrics, or other alignment metrics that measure an alignment of sample sequences with a reference genome. As another example, the base-caller-recalibration system 106 determines forward-reverse-depth metrics (or other such depth metrics) or callability metrics for variant-nucleobase calls (or other such call-quality metrics).

As just mentioned, in some embodiments, the base-caller-recalibration system 106 re-engineers the raw sequencing metrics to generate read-based sequencing metrics 306 that are more informative for comparing metrics associated with a reference nucleotide sequence with metrics associated with various supporting alternative nucleotide reads. For example, the base-caller-recalibration system 106 determines various metrics for a sample sequence in relation to a reference sequence and further determines various metrics for the sample sequence in relation to alternative supporting sequences. In addition, the base-caller-recalibration system 106 performs comparative analyses between metrics associated with the reference sequence and the metrics associated with the alternative supporting reads.

For instance, the base-caller-recalibration system 106 compares how nucleotide bases of a sample nucleotide sequence (e.g., sample genome) map to a reference sequence with how the nucleotide bases map to various alternative supporting reads. In some cases, the base-caller-recalibration system 106 determines mapping qualities associated with the reference sequence to compare with mapping qualities associated with alternative supporting reads. For example, the base-caller-recalibration system 106 determines mapping quality statistics reflecting differences in the distribution of reads supporting a reference sequence versus reads supporting alternative alleles.

In these or other cases, the base-caller-recalibration system 106 determines mismatch counts between the sample sequence and the reference sequence and between the reference sequence and alternative supporting reads. The base-caller-recalibration system 106 further compares the mismatch counts to determine a comparative-mismatch-count metric. Further, the base-caller-recalibration system 106 determines soft-clipping metrics for the sample sequence in relation to the reference sequence and further determines soft-clipping metrics in relation to alternative supporting reads. The base-caller-recalibration system 106 also compares the soft clipping metrics between the reference sequence and the alternative supporting reads to generate a comparative-soft-clipping metric. Further still, the base-caller-recalibration system 106 compares base-call-quality metrics in relation to the reference sequence and alternative supporting reads and/or compares query positions of the sample sequence in relation to the reference sequence with those in relation to alternative supporting reads.

As further illustrated in FIG. 3A, the base-caller-recalibration system 106 utilizes the comparisons and/or other statistical tests to generate the read-based sequencing metrics 306, including: i) a comparative-mapping-quality-distribution metric indicating a mapping quality distribution comparing mapping qualities in relation to the reference sequence and mapping qualities in relation to alternative supporting reads, ii) a comparative-secondary-mapping-alignment metric indicating a comparison between secondary mapping in relation to bases in the reference sequence and bases in alternative supporting reads, iii) a comparative-mismatch-count metric indicating a comparison between mismatched nucleotide bases in relation to the reference sequence and mismatched bases in relation to alternative supporting reads, iv) a comparative-soft-clipping metric indicating a comparison between soft-clipping metrics in relation to the reference sequence and soft-clipping metrics in relation to alternative supporting reads, v) one or more comparative-read-depth metrics indicating comparisons between read depths of the nucleotide reads 302 and one or more average read depths (e.g., local average read depths at a particular genomic coordinate and global average read depths across a number genomic coordinates in a region), vi) one or more comparative-base-quality metric indicating comparisons between base qualities in relation to the reference sequence and base qualities in relation to alternative supporting reads (e.g., for overall base quality, early base quality, and late base quality in the nucleotide reads 302), vii) a comparative-query-position metric indicating a comparison between query positions in relation to the reference sequence and query positions in relation to alternative supporting reads, viii) one or more contextual-information metrics indicating homopolymers and periodicity of nucleotide-base calls, ix) a strand-bias metric indicating a strand bias associated with one or more nucleotide reads 302, and x) a read-direction-bias metric indicating a read direction bias associated with the nucleotide reads 302. In some cases, the base-caller-recalibration system 106 generates or re-engineers additional or alternative read-based sequencing metrics 306.

In addition to the read-based sequencing metrics 306, as illustrated in FIG. 3B, the base-caller-recalibration system 106 generates call-model-generated sequencing metrics 312. In particular, the base-caller-recalibration system 106 generates the call-model-generated sequencing metrics from sequence data 308 utilizing a call-generation model 310. For example, the base-caller-recalibration system 106 extracts or determines sequence data 308 based on the read processing and mapping 304 described in relation to FIG. 3A. In some cases, the base-caller-recalibration system 106 generates the sequence data 308 as part of one or more digital files, such as BCL and FASTQ files.

To generate such files, in some embodiments, the sequencing device 114 (or the base-caller-recalibration system 106) utilizes cluster generation and SBS chemistry to sequence millions or billions of clusters in a flow cell. During SBS chemistry, for each cluster, the sequencing device 114 (or the base-caller-recalibration system 106)

stores nucleotide-base calls from the nucleotide reads 302 for every cycle of sequencing via real-time analysis (RTA) software. The sequencing device 114 (or the base-caller-recalibration system 106) utilizes RTA software to further store base-call data in the form of individual base-call data files (or BCLs). In some cases, the sequencing device 114 (or the base-caller-recalibration system 106) further converts the BCL files into sequence data 308 (e.g., via BCL to FASTQ conversion). For instance, the sequencing device 114 (or the base-caller-recalibration system 106) generates a FASTQ file from the nucleotide reads 302, where the FASTQ file includes sequence data 308.

In some cases, the base-caller-recalibration system 106 generates the sequence data 308 for each cluster that passes an initial quality filter from a sample sequence. For example, the base-caller-recalibration system 106 generates entries for each cluster, where each entry includes four lines (or four items of sequence data): i) a sequence identifier with information about the sequencing run and the cluster, ii) nucleotide-base calls that make up the sequence (e.g., a sequence of A, C, T, G, and/or N calls), iii) a separator (e.g., a "+" sign), and iv) base-call-quality metrics indicating probabilities of correctness for the nucleotide-base calls (Phred +33 encoded).

As further illustrated in FIG. 3B, the base-caller-recalibration system 106 implements, utilizes, or applies the call-generation model 310 to process or analyze the sequence data 308. Indeed, in some embodiments, the base-caller-recalibration system 106 generates the call-model-generated sequencing metrics 312 by utilizing the call-generation model 310 to re-engineer raw sequencing metrics (e.g., raw sequencing metrics within the sequence data 308). In particular, the call-generation model 310 includes mapping-and-alignment components to map and align nucleotide-base calls from the sequence data 308. In addition, the call-generation model 310 includes variant-calling components to generate nucleotide-base calls (e.g., reference-base calls such as variant calls or non-variant calls) from the sequence data 308. In some cases, the base-caller-recalibration system 106 extracts the call-model-generated sequencing metrics 312 that have been generated utilizing the mapping-and-alignment components and the variant-calling components of the call-generation model 310.

To illustrate examples of the call-model-generated sequencing metrics 312, in some cases, the base-caller-recalibration system 106 generates (variant-calling metrics including one or more of: i) a base-call-quality metric (e.g., DRAGEN QUAL score) indicating a quality score for nucleotide-base calls generated via the call-generation model 310, ii) a call-model-generated-foreign-read-detection metric (e.g., foreign read detection (FRD) score) indicating a probability that one or more of the nucleotide reads 302 in a pileup might be foreign reads (e.g., their true location is elsewhere in the reference sequence), iii) a call-model-generated-base-quality-dropoff metric (e.g., base quality dropoff (BQD) score) indicating a probability of base quality dropoff based on one or more of strand bias, error position in a thread, or low mean base quality over a subset of nucleotide reads 302, iv) average read depths, v) indel statistics (e.g., a polymerase chain reaction or "PCR" curve) and/or vi) hidden Markov model (HMM) statistics, vii) a secondary-alignment metric indicating a probability that a secondary nucleotide-base call is correct, viii) a base-context metric indicating contextual information for nucleotide around a nucleotide-base call, iv) a nearby-call metric indicating nearby (e.g., adjacent or within a threshold degree of separation from) a nucleotide-base call, x) a joint-detection metric indicating a probability of detecting a joint corresponding to two or more overlapping nucleotide-base calls, xii) read-filtering metrics indicating threshold quality metrics or other metrics for filtering out nucleotide-base calls with low mapping quality, base quality, or other quality metrics, or others. The base-caller-recalibration system 106 generates the call-model-generated sequencing metrics 312 from internal (e.g., proprietary, and model-specific) variables that reflect interacting processing paths, corner cases, and difficult predictions/decisions.

As indicated above, in some cases, the base-caller-recalibration system 106 determines FRD scores according to the methods described in U.S. patent application Ser. No. 16/280,022 to Eric Jon Ojard, entitled System and Method for Correlated Error Event Mitigation for Variant Calling, which is incorporated by reference herein in its entirety. In certain implementations, the base-caller-recalibration system 106 also (or alternatively) determines BQD scores, FRD scores, HMM statistics, and/or other variant-calling metrics according to the methods described in U.S. patent application Ser. Nos. 17/165,828, 15/643,381, and 14/811,836, which are incorporated by reference herein in their entireties.

As illustrated in FIG. 3B, the call-model-generated sequencing metrics 312 include, but are not limited to, variant-calling metrics extracted via the variant-calling components of the call-generation model 310. In addition or in the alternative to the examples of the call-model-generated sequencing metrics 312 described above, in some cases, the base-caller-recalibration system 106 generates (e.g., via metric re-engineering) variant-calling metrics including one or more of: i) a number of samples in a population, ii) a number of reads processed for generating nucleotide-base calls, a number of variants (e.g., SNPs, indels, and MNPs), iii) a number of biallelic sites (e.g., genomic coordinates that contain two observed alleles), iv) a number of multiallelic sites (e.g., a number of sites in a variant call file that contain three or more observed alleles), v) a number of SNPs, vi) numbers of different types of indels (e.g., homozygous insertions, heterozygous insertions, and heterozygous deletions), vii) a total number of heterozygous indels (e.g., insertion+deletion, insertion+SNP, or deletion+SNP), viii) a number of de novo SNPs (e.g., SNPs with de novo quality metrics that satisfy a threshold level), ix) a number of de novo indels (e.g., indels with de novo quality metrics that satisfy a threshold level), x) a number of de novo MNPs (e.g., MNPs with de novo quality metrics that satisfy a threshold level, xi) a number of SNPs in a first chromosome divided by a number of SNPs in a second chromosome, xii) a number of SNP transitions, xiii) a number of SNP transversions, xiv) a number of heterozygous variants, xv) a number of homozygous variants, xvi) a ratio between the number of heterozygous variants and the number of homozygous variants, xvii) a number of variants detected within a dbSNP reference file, and/or xviii) a total number of variants minus the number detected within the dbSNP file.

Additionally, the call-model-generated sequencing metrics 312 can include mapping-and-alignment sequencing metrics extracted via the mapping-and-alignment components of the call-generation model 310. For instance, the base-caller-recalibration system 106 generates or extracts (e.g., via metric re-engineering) mapping-and-alignment metrics including one or more of: i) a number of total input reads, ii) a number of duplicate marked reads, iii) a number of duplicate marked and mate reads removed, iv) a number of unique reads, v) a number of reads with mate sequenced, vi) a number of reads without mate sequenced, vii) indications of reads that fail quality checks, viii) indications of mapped reads, ix) a number of unique and mapped reads, x) a number of unmapped reads, xi) a number of singleton reads (e.g., where the read is mapped but the paired mate could not be read), xii) a number of paired reads, xiii) a number of properly paired reads (e.g., where both reads in a pair are mapped and fall within an acceptable range from each other based on an estimated insert length distribution), xiv) a number of discordant reads (e.g., not properly paired reads), xv) a number of paired reads mapped to different chromosomes, xvi) a number of paired reads mapped to different chromosomes that also have a mapping-quality metric of 10 or greater, xvii) percentages of reads within indels R1 and R2, xviii) percentages of bases in R1 and R2 that are soft clipped, xix) a numbers of mismatched bases in R1 and R2, xx) a number of bases with a base quality of at least 30 (e.g., total and/or in R1 or R2), xxi) a number of alignments (e.g., total alignments, secondary alignments, and/or supplementary alignments), xxii) an estimated read length, and xxiii) an estimated sample contamination.

Turning now to FIG. 3C, as illustrated in that figure, the base-caller-recalibration system 106 generates, extracts, or determines externally sourced sequencing metrics 316. In particular, the base-caller-recalibration system 106 determines externally sourced sequencing metrics 316 from one or more databases external to the base-caller-recalibration system 106, such as a sequencing information database 314 (e.g., the database 116). For example, the base-caller-recalibration system 106 accesses sequencing metrics that are generic or applicable to sequencing nucleotides generally. In addition, the base-caller-recalibration system 106 accesses or determines sequencing information about a particular reference sequence (e.g., stored within the sequencing information database 314). In some cases, the base-caller-recalibration system 106 determines externally sourced sequencing metrics 316 including: i) a mappability metric indicating an ease or difficult of mapping a particular nucleotide sequence (or a particular nucleotide read or nucleotide-base call), ii) a guanine-cytosine-content metric indicating a count (or a dropout or a mean) of guanine-cytosine content in a reference nucleotide sequence (e.g., reference genome), iii) a replication-timing metric indicating a time required to replicate a particular number of nucleotides from a reference sequence, iv) one or more DNA-structure-metrics indicating DNA structures of a reference sequence (e.g., reference genome), v) a conservation metric indicating a measure of sequence conservation across multiple species (e.g., a measure of change relative to an average), and/or others.

Figure 4:
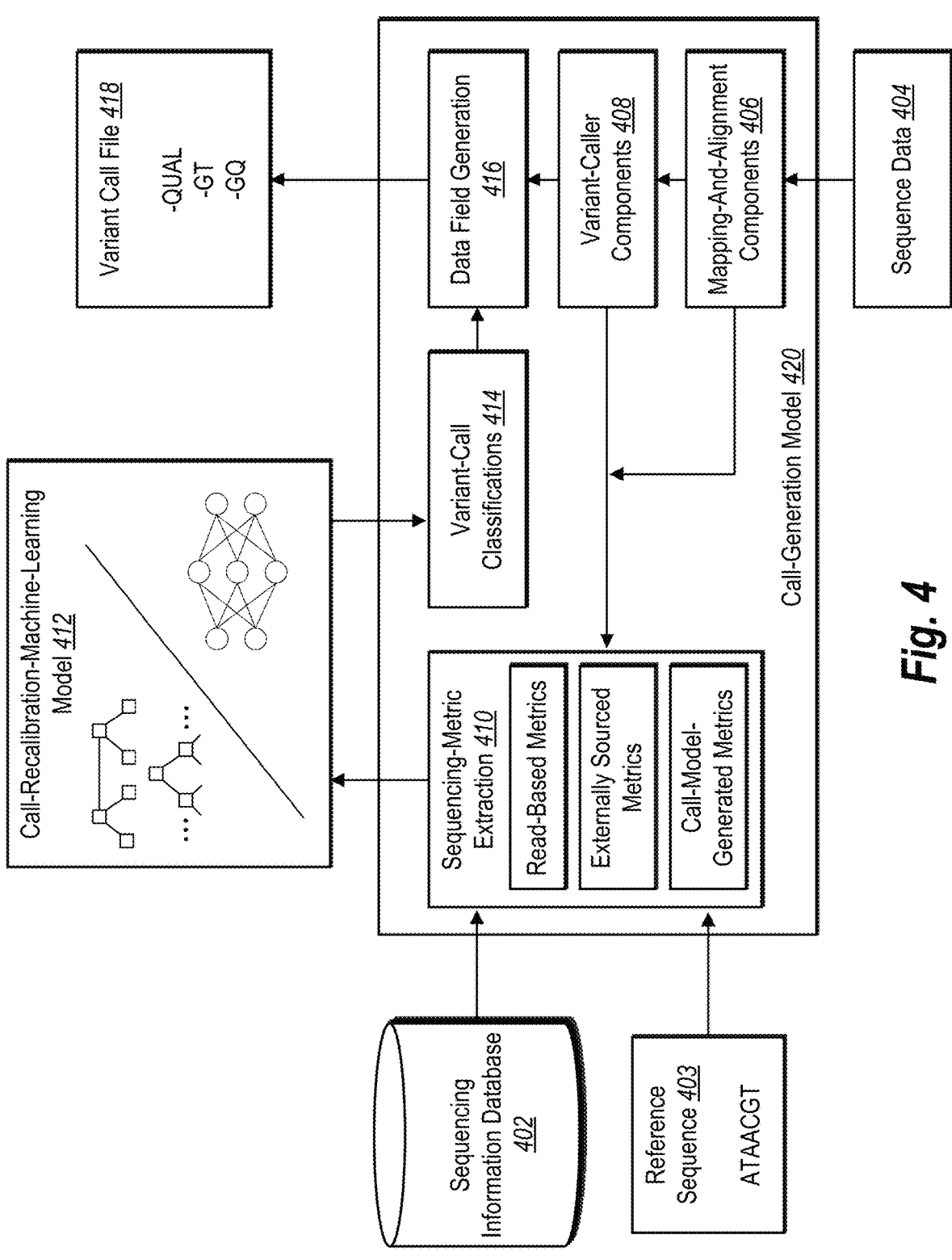
FIG. 4 illustrates generating variant-call classifications and recalibrating a nucleotide-base call utilizing a call-recalibration-machine-learning model in accordance with one or more embodiments.

As mentioned, in certain described embodiments, the base-caller-recalibration system 106 utilizes a call-recalibration-machine-learning model together with a call-generation model to generate a nucleotide-base call. In particular, the base-caller-recalibration system 106 utilizes the call-recalibration-machine-learning model to modify data fields corresponding to a variant call file representing a nucleotide-base call. FIG. 4 illustrates generating a nucleotide-base call by modifying a variant call file utilizing a call-recalibration-machine-learning model and call-generation model in accordance with one or more embodiments.

As illustrated in FIG. 4, the base-caller-recalibration system 106 accesses a sequencing information database 402 (e.g., the sequencing information database 314), a reference sequence 403, and sequence data 404 (e.g., the sequence data 308) extrapolated from one or more nucleotide reads. Indeed, the base-caller-recalibration system 106 performs sequencing-metric extraction 410 to extract or re-engineer sequencing metrics as described above in relation to FIGS.

3A-3C. For example, the base-caller-recalibration system 106 generates read-based sequencing metrics, externally sourced sequencing metrics, and call-model-generated sequencing metrics. In some cases, the base-caller-recalibration system 106 utilizes mapping-and-alignment components 406 of a call-generation model 420 (e.g., the call-generation model 310) to determine mapping-and-alignment sequencing metrics as described above. In addition, the base-caller-recalibration system 106 utilizes variant-caller components 408 of the call-generation model 420 to generate variant-calling metrics as described above. Further, the base-caller-recalibration system 106 determines read-based sequencing metrics and externally source sequencing metrics as well (e.g., from sequencing information database 402 and/or the reference sequence 403).

As further illustrated in FIG. 4, the base-caller-recalibration system 106 generates variant-call classifications 414. More specifically, the base-caller-recalibration system 106 utilizes a call-recalibration-machine-learning model 412 to generate the variant-call classifications 414 from the sequencing metrics. For example, the call-recalibration-machine-learning model 412 generates variant-call classification 414 including a false-positive classification, a genotype-error classification, and a true-positive classification. Specifically, the false-positive classification indicates a probability that a nucleotide-base call (e.g., a variant call) is a false positive. Conversely, a true-positive classification indicates a probability that a nucleotide-base call (e.g., a variant call) is a true positive. Additionally, a genotype-error classification indicates a probability of error associated with a genotype for a nucleotide-base call (e.g., a variant call).

In some cases, the call-recalibration-machine-learning model 412 is an ensemble of gradient boosted trees that processes the sequencing metrics to generate the variant-call classifications 414. For instance, the call-recalibration-machine-learning model 412 includes a series of weak learners such as non-linear decision trees that are trained in a logistic regression to generate the variant-call classifications 414. In some cases, the call-recalibration-machine-learning model 412 includes metrics within various trees that define how the call-recalibration-machine-learning model 412 processes the sequencing metrics to generate the variant-call classifications 414. Additional detail regarding the training of the call-recalibration-machine-learning model 412 is provided below with reference to FIG. 5.

In certain embodiments, the call-recalibration-machine-learning model 412 is a different type of machine learning model such as a neural network, a support vector machine, or a random forest. For example, in cases where the call-recalibration-machine-learning model 412 is a neural network, the call-recalibration-machine-learning model 412 includes one or more layers each with neurons that make up the layer for processing the sequencing metrics. In some cases, the call-recalibration-machine-learning model 412 generates the variant-call classifications 414 by extracting latent vectors from the sequencing metrics, passing the latent vectors from layer to layer (or neuron to neuron) to manipulate the vectors until utilizing an output layer (e.g., one or more fully connected layers) to generate the variant-call classifications 414 (e.g., as a set of three separate classifications).

As suggested above, in some embodiments, the base-caller-recalibration system 106 can utilize multiple call-recalibration-machine-learning models together. For example, the base-caller-recalibration system 106 utilizes the call-recalibration-machine-learning model 412 to generate a first set of variant-call classifications and further utilizes a second call-recalibration-machine-learning model (e.g., with the same or a different architecture) to generate a second set of variant-call classifications. For example, the base-caller-recalibration system 106 utilizes two (or more) different call-recalibration-machine-learning models in parallel, each trained with different random seeds (e.g., for different biases to process data differently), resulting in different variant-call classifications from the same sequencing metrics.

In some embodiments, the base-caller-recalibration system 106 further generates a combined set of variant-call classifications from the different variant-call classifications generated via the different call-recalibration-machine-learning models. In some cases, the base-caller-recalibration system 106 generates variant-call classifications (e.g., the variant-call classifications 414) from a first set and a second set of variant-call classifications generated from a first call-recalibration-machine-learning model and a second call-recalibration-machine-learning model, respectively. For instance, the base-caller-recalibration system 106 determines an average or a weighted combination of the first and second set of variant-call classifications to generate the combined variant-call classifications for recalibrating a nucleotide-base call. In some embodiments, the base-caller-recalibration system 106 determines a mean for each variant-call classification across each call-recalibration-machine-learning model and renormalizes the mean variant-call classification. In other embodiments, the base-caller-recalibration system 106 learns linear weights and adapts the weights to minimize overall error or loss for the variant-call classifications. In still other embodiments, the base-caller-recalibration system 106 weights the variant-call classifications for each call-recalibration-machine-learning model based on the inverse of average error across the models.

In one or more implementations, the base-caller-recalibration system 106 further utilizes a metamodel subsequent to the call-recalibration-machine-learning models. For example, the base-caller-recalibration system 106 utilizes a classification-combiner-machine-learning model to combine variant-call classifications generated from each call-recalibration-machine-learning model—such as by selecting weights to apply to the variant-call classifications generated by each call-recalibration-machine-learning model. Indeed, in some cases, the base-caller-recalibration system 106 trains the classification-combiner-machine-learning model to determine, select, or predict respective weights for call-recalibration-machine-learning models to result in a highest accuracy or a minimized loss.

When generating the variant-call classifications 414, in some embodiments, the base-caller-recalibration system 106 generates variant-call classifications by utilizing statistics to summarize a mapping quality distribution (e.g., a comparative-mapping-quality-distribution metric) of reference supporting reads and alternative supporting reads. For example, the base-caller-recalibration system 106 can determine and utilize the mean of the MAPQ for reads supporting an alternative allele as a variant-call classification. In these or other embodiments, the recalibration-machine-learning model 412 learns from the data that, when the MAPQ of an alternative allele is low and a depth metric is high relative to other MAPQ and depth metrics in distributions, a resultant nucleotide-base call is more likely to be a false positive variant. Indeed, as the probability of a false positive variant increases, the MAPQ metrics would likely decrease.

As a further example of generating the variant-call classifications 414 utilizing the call-recalibration-machine-learning model 412, in some cases, the base-caller-recalibration system 106 compares a mapping quality (e.g., MAPQ) associated with a nucleotide read (e.g., from the sequencing metrics) with a mapping-quality threshold. For instance, the base-caller-recalibration system 106 utilizes a mapping-quality threshold such as a threshold difference between best and second-best alignment scores. Upon determining that the mapping quality does not satisfy the threshold, the base-caller-recalibration system 106 adjusts one or more of the variant-call classifications 414 accordingly. For instance, the base-caller-recalibration system 106 increases a probability of genotype error and/or false positive error based on whether the mapping quality satisfies the corresponding threshold.

In addition (or in the alternative) to the method of generating the variant-call classifications 414 just described, the base-caller-recalibration system 106 can (i) utilize an accumulation of statistical analyses over complex functions (depending on the architecture of the recalibration-machine-learning model 412) to determine how to best fit the data (e.g., based on relationship between the various metrics) or (ii) compare other metrics, such as read depth, base quality, or others associated with a nucleotide-base call (e.g., from the sequencing metrics) with corresponding thresholds. The base-caller-recalibration system 106 further generates variant-call classifications 414 accordingly. For example, in some embodiments, the base-caller-recalibration system 106 trains the recalibration-machine-learning model 412 to minimize a loss generated from a number of (different types of) sequencing metrics to determine weights and biases that best fit the data (e.g., that result in a reduced or minimized loss) for generating the variant-call classifications 414. As another example, upon determining that a read depth fails to satisfy a read-depth threshold (e.g., a maximum read depth corresponding to a particular genomic coordinate or generally across all genomic coordinates), the base-caller-recalibration system 106 increases a genotype-error probability and/or increases or decreases a false-positive probability and a true-positive probability for a corresponding nucleotide-base call.

In addition to generating the variant-call classifications 414, as further illustrated in FIG. 4, the base-caller-recalibration system 106 performs data field generation 416. More specifically, the base-caller-recalibration system 106 generates data fields for a nucleotide-base call corresponding to a variant call file utilizing the variant-caller components 408 of the call-generation model 420 and modifies or maintains values for such data fields based the variant-call classifications 414. For instance, the base-caller-recalibration system 106 modifies various metrics such as quality metrics, mapping metrics, or other metrics associated with the nucleotide-base call. In certain embodiments, the nucleotide-base call is represented or defined by the variant call file 418 which includes metrics corresponding to the data fields, such as a call-quality metric corresponding to a call-quality field, a genotype metric corresponding to a genotype field, and a genotype-quality metric corresponding to a genotype-quality field.

In certain embodiments, the base-caller-recalibration system 106 generates (data fields for) a nucleotide-base call utilizing the variant-caller components 408 together with the variant-call classifications 414. For instance, the base-caller-recalibration system 106 generates, utilizing the variant-caller components 408, data fields for various metrics of a nucleotide-base call such as nucleotide(s) included in the call, a call quality (QUAL), a genotype (GT), and a genotype quality (GQ).

In addition to generating a nucleotide-base call via the call-generation model 420, the base-caller-recalibration system 106 also recalibrates or modifies the nucleotide-base call via the variant-call classifications 414 from the call-recalibration-machine-learning model 412. In one or more implementations, the base-caller-recalibration system 106 modifies the nucleotide-base call by modifying or recalibrating data fields for one or more of the metrics associated with the nucleotide-base call (e.g., as included within the variant call file 418). For example, the base-caller-recalibration system 106 determines updated values for metrics such as the call quality, the genotype, and the genotype quality from the variant-call classifications 414. Indeed, the base-caller-recalibration system 106 combines or compares the variant-call classifications 414 to recalibrate the corresponding metrics of the nucleotide-base call included in the variant call file 418.

To update or recalibrate the call-quality metric associated with a nucleotide-base call, the base-caller-recalibration system 106 determines how each of the variant-call classifications 414 impact or affect the base-call-quality metric and adjusts the base-call-quality metric accordingly. For example, the base-caller-recalibration system 106 determines that a high probability for a genotype error results in a lower overall genotype quality and possibly a different overall call quality. As another example, the base-caller-recalibration system 106 determines that a high probability for a false positive variant results in a lower overall call quality. As yet another example, the base-caller-recalibration system 106 determines that a high probability for a true positive variant results in a higher overall (variant) call quality. As a further example, if the base-caller-recalibration system 106 determines a high probability for a genotype error (e.g., higher than for the other two variant-call classifications 414), then the base-caller-recalibration system 106 determines that nucleotide-base call is most likely a true variant with the wrong genotype. The base-caller-recalibration system 106 accordingly updates the genotype along with the genotype quality and the call quality associated with the nucleotide-base call.

In one or more implementations, the base-caller-recalibration system 106 generates a combination (e.g., a weighted combination or an average) of the variant-call classifications 414 to recalibrate the call-quality metric. In particular, the base-caller-recalibration system 106 weights the false-positive classification, the genotype-error classification, and the true-positive classification according to their respective impact on (variant) call quality. In some cases, the base-caller-recalibration system 106 weights each variant-call classification evenly, while in other cases the base-caller-recalibration system 106 determines different weights for each variant-call classification. In any event, the base-caller-recalibration system 106 determines a weighted combination or a weighted average of the variant-call classifications 414 to recalibrate (increase or decrease) a call-quality metric for a nucleotide-base call (e.g., an initial variant call).

To update or recalibrate the genotype metric (e.g., within the GT field of the variant call file 418) associated with a nucleotide-base call, the base-caller-recalibration system 106 utilizes one or more of the variant-call classifications 414. For example, the base-caller-recalibration system 106 compares the three variant-call classifications 414 (e.g., the false-positive classification, the genotype-error classification, and the true-positive classification) to determine which of the variant-call classifications 414 has a highest probability. In some cases, the base-caller-recalibration system 106 utilizes the variant-call classification with the highest probability to recalibrate the genotype metric (e.g., from 0 as corresponding to the reference base to 1 as corresponding to a first alternative supporting read). For instance, if the base-caller-recalibration system 106 determines a highest probability for the false-positive classification, then the base-caller-recalibration system 106 recalibrates the genotype metric accordingly. As another example, if the base-caller-recalibration system 106 determines a highest probability for the true-positive classification, then the base-caller-recalibration system 106 recalibrates (or refrains from recalibrating) the genotype metric.

In other embodiments, the base-caller-recalibration system 106 utilizes only the genotype-error probability to modify the genotype metric. For example, if the base-caller-recalibration system 106 determines a high genotype-error probability, then the base-caller-recalibration system 106 recalibrates the genotype metric to indicate a different genotype of a nucleotide-base call.

To update or recalibrate the genotype-quality metric (e.g., within the GQ field of the variant call file 418) associated with a nucleotide-base call, the base-caller-recalibration system 106 utilizes one or more of the variant-call classifications 414. More specifically, the base-caller-recalibration system 106 determines how each of the variant-call classifications 414 affect the genotype-quality metric and recalibrates the genotype-quality metric accordingly (e.g., by increasing or decreasing the quality score between 0 to 10 or 0 to 100 or on some other scale). For example, the base-caller-recalibration system 106 determines that a higher genotype-error probability (generally) indicates a lower genotype-quality metric, and the base-caller-recalibration system 106 reduces the metric accordingly.

In some cases, the base-caller-recalibration system 106 determines a combination (e.g., a weighted combination or a weighted average) of the variant-call classifications 414 to modify the genotype-quality metric. For example, the base-caller-recalibration system 106 determines a combined effect that the variant-call classifications 414 have on the genotype-quality metric. As another example, the base-caller-recalibration system 106 determines individual impacts that each variant-call classification has on the genotype-quality metric and weights each variant-call classification accordingly. The base-caller-recalibration system 106 further recalibrates the genotype-quality metric by increasing or decreasing its value based on the indicated probabilities associated with each of the variant-call classifications 414.

As described, the base-caller-recalibration system 106 generates variant-call classifications 414 and a nucleotide-base call from the same set of sequencing metrics (or a subset of the sequencing metrics that are shared between the call-recalibration-machine-learning model 412 and the call-generation model 420). Indeed, the base-caller-recalibration system 106 utilizes the call-recalibration-machine-learning model 412 to generate the variant-call classifications 414 from sequencing metrics while also generating a nucleotide-base call for a sample sequence. Indeed, the base-caller-recalibration system 106 can operate the call-recalibration-machine-learning model 412 in parallel with the call-generation model 420 to generate metrics for a nucleotide-base call and variant-call classifications 414 for recalibrating the generated metrics.

As further illustrated in FIG. 4, the base-caller-recalibration system 106 generates a variant call file 418. In particular, the base-caller-recalibration system 106 generates a variant call file 418 that represents or defines a nucleotide-base call from the sequencing metrics corresponding to a genomic coordinate. As shown, the variant call file 418 includes various call metrics such as a call-quality metric (QUAL), a genotype metric (GT), and a genotype-quality metric (GQ). To generate the variant call file 418, as described, the base-caller-recalibration system 106 generates metrics for a nucleotide-base call utilizing the call-generation model 420 and recalibrates the nucleotide-base call utilizing the variant-call classifications 414 from the call-recalibration-machine-learning model 412.

In one or more implementations, the base-caller-recalibration system 106 updates or otherwise modifies the data fields for the variant call file 418 according to particular algorithms. After modifying such data fields, the base-caller-recalibration system 106 can generate the variant call file 418 (e.g., a post-filter variant call file) to include metrics reflecting the updated data fields for QUAL, GT, and GQ. For instance, in some cases, the base-caller-recalibration system 106 updates the QUAL field for every variant based on the probability of a false-positive variant (e.g., the false-positive classification). As indicated above, in some cases, QUAL indicates the probability that there is some kind of variant (or other nucleotide-base call) at a given location, measured in PHRED scale.

In addition, if the base-caller-recalibration system 106 determines that the highest probability from among the three variant-call classifications 414 is the genotype-error classification (e.g., the probability of a het/hom error), then the base-caller-recalibration system 106 updates the GQ field while preserving or maintaining the GT field. Specifically, in some embodiments, the base-caller-recalibration system 106 updates the GQ field based on the true-positive classification (e.g., the probability of a true genotype).

Further, if the base-caller-recalibration system 106 determines that the highest probability from among the variant-call classifications 414 is the true-positive classification, in some cases, the base-caller-recalibration system 106 updates both the GQ field and the GT field. Specifically, the base-caller-recalibration system 106 updates the GQ field based on the genotype-error classification and further updates the GT field to switch the genotype depending on whether the existing GT is 0/X or X/X (where X is a non-zero value).

If the base-caller-recalibration system 106 determines that neither the true-positive classification nor the genotype-error classification has the highest probability among the variant-call classifications 414, in some embodiments, the base-caller-recalibration system 106 updates the GQ field. In other words, if the base-caller-recalibration system 106 determines that the false-positive classification has the highest probability, the base-caller-recalibration system 106 updates the GQ field. In particular, the base-caller-recalibration system 106 updates the GQ field based on the probability indicated by the true-positive classification.

As suggested above, in some embodiments, the base-caller-recalibration system 106 increases or decreases a base-call-quality metric (e.g., Q score) for a nucleotide-base call. Based on the variant-call classifications 414, for example, the base-caller-recalibration system 106 increases base-call-quality metrics for nucleotide-base calls that would not have previously passed a quality filter and determines that the increased base-call-quality metrics now passes the quality filter. In some such cases, the base-caller-recalibration system 106 includes nucleotide-base calls with such increased base-call-quality metrics (passing the quality filter) in a post-filter variant call file. By contrast, in other cases, the base-caller-recalibration system 106 decreases base-call-quality metrics for nucleotide-base calls that previously would have passed a quality filter and determines that the decreased base-call-quality metrics now fail the quality filter. In some such cases, the base-caller-recalibration system 106 excludes nucleotide-base calls with decreased base-call-quality metrics (failing the quality filter) from a post-filter variant call file, but includes the nucleotide-base calls with such decreased base-call-quality metrics in a pre-filter variant call file.

For example, the base-caller-recalibration system 106 can remove false positive variant calls and recover false negative variant calls by changing corresponding base-call-quality metrics. To remove a false positive, in some cases, the base-caller-recalibration system 106 decreases the base-call-quality metric of a nucleotide-base call that initially passed a quality filter-based on the variant-call classifications 414 from the call-recalibration-machine-learning model 412. Based on determining the decreased base-call-quality metric falls below a threshold metric (e.g., a Q score of 3.0 or 10.0), the base-caller-recalibration system 106 determines that the nucleotide-base call no longer passes the quality filter. The base-caller-recalibration system 106 thus filters out, or removes, the false-positive-nucleotide-base call that initially passed the filter by changing its base-call-quality metric.

In addition to removing false positives based on changes to base-call-quality metrics, the base-caller-recalibration system 106 can remove false positive variant calls based on changes to genotype. To remove a false positive, in some cases, the base-caller-recalibration system 106 changes a genotype of an initial nucleotide-base call indicating a different nucleotide base than a reference base (e.g., GT=1 or 2) to a genotype of an updated nucleotide-base call indicating a same nucleotide base as the reference base (e.g., GT=0)—based on the variant-call classifications 414 from the call-recalibration-machine-learning model 412. Based on the genotype being the same as the reference base, the base-caller-recalibration system 106 does not identify the nucleotide-base call as a variant and, in some cases, excludes data for the nucleotide-base call from a variant call file.

To recover a false negative, the base-caller-recalibration system 106 increases the base-call-quality metric of a nucleotide-base call that initially failed a quality filter-based on the variant-call classifications 414 from the call-recalibration-machine-learning model 412. Based on determining the increased base-call-quality metric exceeds a threshold metric, the base-caller-recalibration system 106 determines that the nucleotide-base call passes the quality filter. The base-caller-recalibration system 106 thus recovers a false-negative-nucleotide-base call that was initially filtered out by changing its base-call-quality metric.

In addition to recovering false negatives based on changes to base-call-quality metrics, the base-caller-recalibration system 106 can recover false negative variant calls based on changes to genotype. To recover a false negative, in some cases, the base-caller-recalibration system 106 changes a genotype of an initial nucleotide-base call indicating the same nucleotide base as a reference base (e.g., GT=0) to a different genotype of an updated nucleotide-base call indicating a different nucleotide base than the reference base (e.g., GT=1 or 2)—based on the variant-call classifications 414 from the call-recalibration-machine-learning model 412. Based on the differing genotype of the updated nucleotide-base call and a passing base-call-quality metric, the base-caller-recalibration system 106 identifies the nucleotide-base call as a variant and includes the nucleotide-base call within a variant call file.

Indeed, in some implementations, the base-caller-recalibration system 106 operates in a specific sequential order utilizing the call-generation model 420 and the call-recalibration-machine-learning model 412. For example, the base-caller-recalibration system 106 generates a FASTQ file by converting a BCL file to FASTQ. In addition, the base-caller-recalibration system 106 (subsequently) utilizes the mapping-and-alignment components 406 of the call-generation model 420 to map and align nucleotide bases from a sample nucleotide sequence. In some cases, the base-caller-recalibration system 106 maps and aligns the nucleotide bases of the sample sequence in relation to a reference sequence (e.g., reference genome) and/or various alternative supporting reads.

After mapping and aligning, as described herein, the base-caller-recalibration system 106 then utilizes the variant-caller components 408 of the call-generation model 420 to generate an initial nucleotide-base call for the sample sequence corresponding to a particular genomic coordinate-based on various sequencing metrics. After or at the same time, the base-caller-recalibration system 106 also applies the call-recalibration-machine-learning model 412 to generate the variant-call classifications 414 from sequencing metrics extracted via the mapping and aligning, the variant calling, and/or from other sources as described above. Based on the variant-call classifications 414, the base-caller-recalibration system 106 recalibrates the nucleotide-base call (e.g., by modifying various data fields corresponding to specific metrics of the nucleotide-base call such as QUAL, GT, and GQ).

In some cases, the base-caller-recalibration system 106 further applies a quality filter to the nucleotide-base call to determine whether the nucleotide-base call passes the quality filter (e.g., a hard pass filter of Q20 or other Q score). The base-caller-recalibration system 106 subsequently identifies a subset of nucleotide-base calls that represent variants from reference bases and pass the quality filter. The base-caller-recalibration system 106 further generates a modified or updated variant call file (e.g., the variant call file 418) that includes the subset of nucleotide-base calls and recalibrated metrics for the subset of nucleotide-base calls, such as updated QUAL metrics, updated GT metrics, and/or updated GQ metrics.

Figure 5:
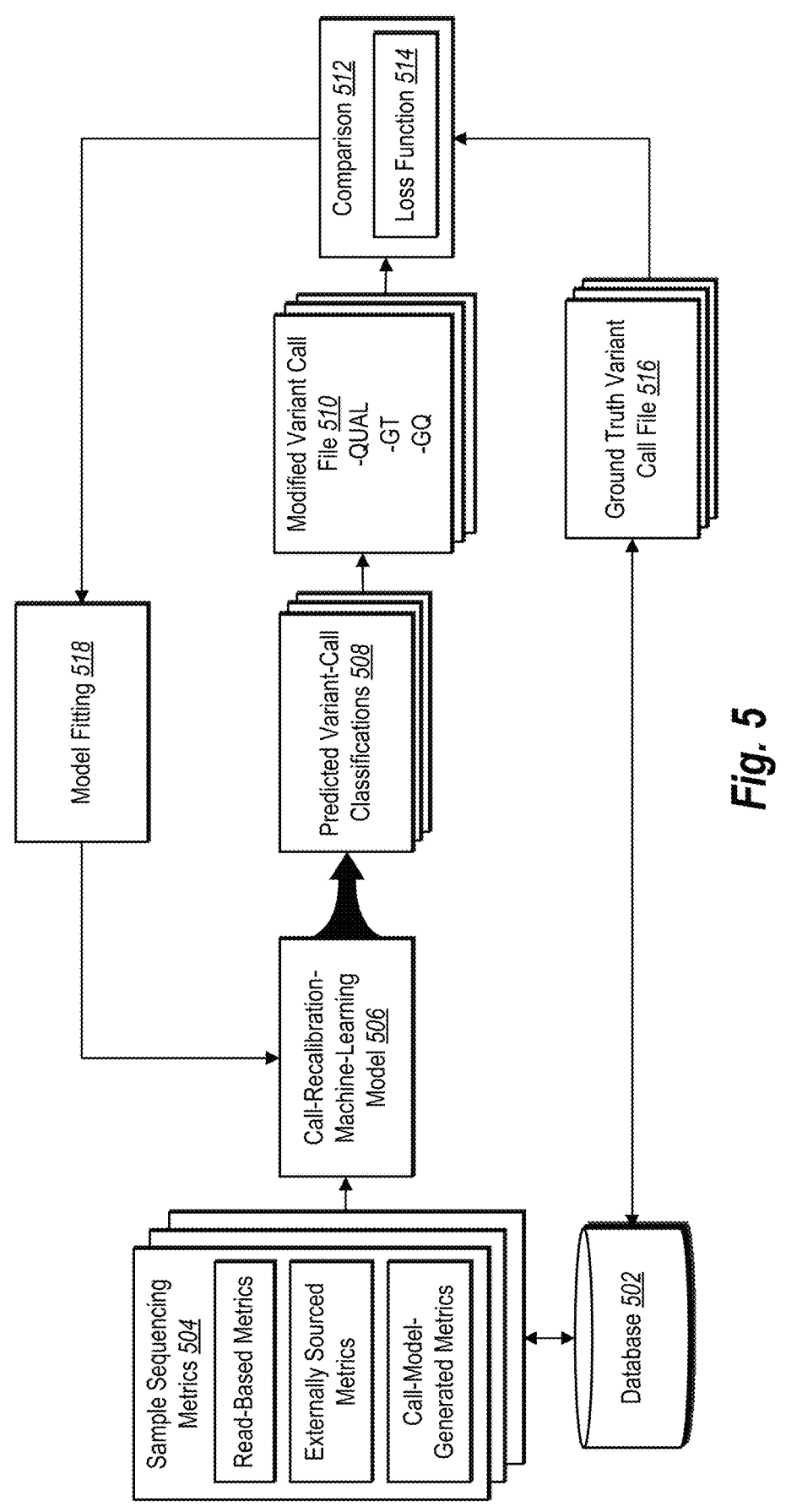
FIG. 5 illustrates an example process for training a call-recalibration-machine-learning model in accordance with one or more embodiments.

As mentioned above, in certain embodiments, the base-caller-recalibration system 106 trains or tunes a call-recalibration-machine-learning model (e.g., the call-recalibration-machine-learning model 412). In particular, the base-caller-recalibration system 106 utilizes an iterative training process to fit a call-recalibration-machine-learning model by adjusting or adding decision trees or learning parameters that result in accurate variant-call classifications (e.g., variant-call classifications 414). FIG. 5 illustrates training a call-recalibration-machine-learning model in accordance with one or more embodiments.

As illustrated in FIG. 5, the base-caller-recalibration system 106 accesses sample sequencing metrics 504 from a database 502 (e.g., the database 116). For example, the base-caller-recalibration system 106 accesses sample sequencing metrics including sample read-based metrics, sample externally sourced sequencing metrics, and sample call-model-generated sequencing metrics. In some cases, the sample sequencing metrics 504 have a corresponding ground truth variant call file 516 associated with them, where the ground truth variant call file 516 indicates an actual nucleotide-base call and its various metrics that result from the set of sequencing metrics 504. For instance, the base-caller-recalibration system 106 utilizes sample sequencing metrics 504 and ground truth variant call files from a training dataset from the food and drug administration, called the PrecisionFDA dataset. In some cases, the sample sequencing metrics 504 include a subset of sample sequencing metrics for each nucleotide-base call in a ground truth variant call file. The ground truth variant call file can have a ground truth variant call (e.g., genotype metric in a genotype field) corresponding to each subset of sample sequencing metrics.

As further illustrated in FIG. 5, the base-caller-recalibration system 106 generates predicted variant-call classifications 508 based on the sample sequencing metrics 504. Specifically, the base-caller-recalibration system 106 utilizes a call-recalibration-machine-learning model 506 (e.g., the call-recalibration-machine-learning model 412) to generate the predicted variant-call classifications 508. Indeed, in some embodiments, the call-recalibration-machine-learning model 506 generates a set of three predicted variant-call classifications 508 including a predicted false-positive classification, a predicted genotype-error classification, and a predicted true-positive classification. The variant-call classifications 508 can accordingly take the form of any of the variant-call classifications described above.

Based on the variant-call classifications 508, the base-caller-recalibration system 106 determines nucleotide-base calls and generates a modified variant call file 510 comprising the nucleotide-base calls and corresponding fields. As indicated above, the base-caller-recalibration system 106 can utilize (i) a call-generation model to generate an initial nucleotide-base call and (ii) the call-recalibration-machine-learning model 506 to modify data fields corresponding to a variant call file for the nucleotide-base call. Such modified or recalibrated values are output in the modified variant call file 510 by, for example the call-generation model. For example, the base-caller-recalibration system 106 determines recalibrated values for particular metrics within the modified variant call file 510, including a call-quality metric (QUAL), a genotype metric (GT), and a genotype-quality metric (GQ).

As further illustrated in FIG. 5, the base-caller-recalibration system 106 performs a comparison 512. Specifically, the base-caller-recalibration system 106 performs the comparison 512 between (i) variant-nucleotide-base calls and/or data fields in the modified variant call file 510 and (ii) variant-nucleotide-base calls and/or data fields in the ground truth variant call file 516. In some embodiments, the base-caller-recalibration system 106 utilizes a loss function 514 to compare variant-nucleotide-base calls and/or data fields from the two variant call files (e.g., to determine an error or a measure of loss between them). For instance, in cases where the call-recalibration-machine-learning model 506 is an ensemble of gradient boosted trees, the base-caller-recalibration system 106 utilizes a mean squared error loss function (e.g., for regression) and/or a logarithmic loss function (e.g., for classification) as the loss function 514.

By contrast, in embodiments where the call-recalibration-machine-learning model 506 is a neural network, the base-caller-recalibration system 106 can utilize a cross entropy loss function, an L1 loss function, or a mean squared error loss function as the loss function 514. For example, the base-caller-recalibration system 106 utilizes the loss function 514 to determine a difference between variant-nucleotide-base calls and/or data fields from the modified variant call file 510 and the ground truth variant call file 516.

As further illustrated in FIG. 5, the base-caller-recalibration system 106 performs model fitting 518. In particular, the base-caller-recalibration system 106 fits the call-recalibration-machine-learning model 506 based on the comparison 512. For instance, the base-caller-recalibration system 106 performs modifications or adjustments to the call-recalibration-machine-learning model 506 to reduce the measure of loss from the loss function 514 for a subsequent training iteration.

For gradient boosted trees, for example, the base-caller-recalibration system 106 trains the call-recalibration-machine-learning model 506 on the gradients of the errors determined by the loss function 514. For instance, the base-caller-recalibration system 106 solves a convex optimization problem (e.g., of infinite dimensions) while regularizing the objective to avoid overfitting. In certain implementations, the base-caller-recalibration system 106 scales the gradients to emphasize corrections to under-represented classes (e.g., where there are significantly more true positives than false positives).

In some embodiments, the base-caller-recalibration system 106 adds a new weak learner (e.g., a new boosted tree) to the call-recalibration-machine-learning model 506 for each successive training iteration as part of solving the optimization problem. For example, the base-caller-recalibration system 106 finds a feature (e.g., a sequencing metric) that minimizes a loss from the loss function 514 and either adds the feature to the current iteration's tree or starts to build a new tree with the feature.

In addition or in the alternative to gradient boosted decision trees, the base-caller-recalibration system 106 trains a logistic regression to learn parameters for generating one or more variant-call classifications such as a true-positive classification. To avoid overfitting, the base-caller-recalibration system 106 further regularizes based on hyper-parameters such as the learning rate, stochastic gradient boosting, the number of trees, the tree-depth(s), complexity penalization, and L1/L2 regularization.

In embodiments where the call-recalibration-machine-learning model 506 is a neural network, the base-caller-recalibration system 106 performs the model fitting 518 by modifying internal parameters (e.g., weights) of the call-recalibration-machine-learning model 506 to reduce the measure of loss for the loss function 514. Indeed, the base-caller-recalibration system 106 modifies how the call-recalibration-machine-learning model 506 analyzes and passes data between layers and neurons by modifying the internal network parameters. Thus, over multiple iterations, the base-caller-recalibration system 106 improves the accuracy of the call-recalibration-machine-learning model 506.

Indeed, in some cases, the base-caller-recalibration system 106 repeats the training process illustrated in FIG. 5 for multiple iterations. For example, the base-caller-recalibration system 106 repeats the iterative training by selecting a new set of sequencing metrics for each nucleotide-base call along with a corresponding ground truth nucleotide-base call in a corresponding ground truth variant call file. The base-caller-recalibration system 106 further generates a new set of predicted variant-call classifications for each iteration along with a new modified variant call file. As described above, the base-caller-recalibration system 106 also compares a variant-nucleotide-base calls and/or data fields from the modified variant call file at each iteration with the corresponding variant-nucleotide-base calls and/or data fields from the corresponding ground truth variant call file and further performs model fitting 518. The base-caller-recalibration system 106 repeats this process until the call-recalibration-machine-learning model 506 generates predicted variant-call classifications that result in variant calls that satisfies a threshold measure of loss.

Figure 6:
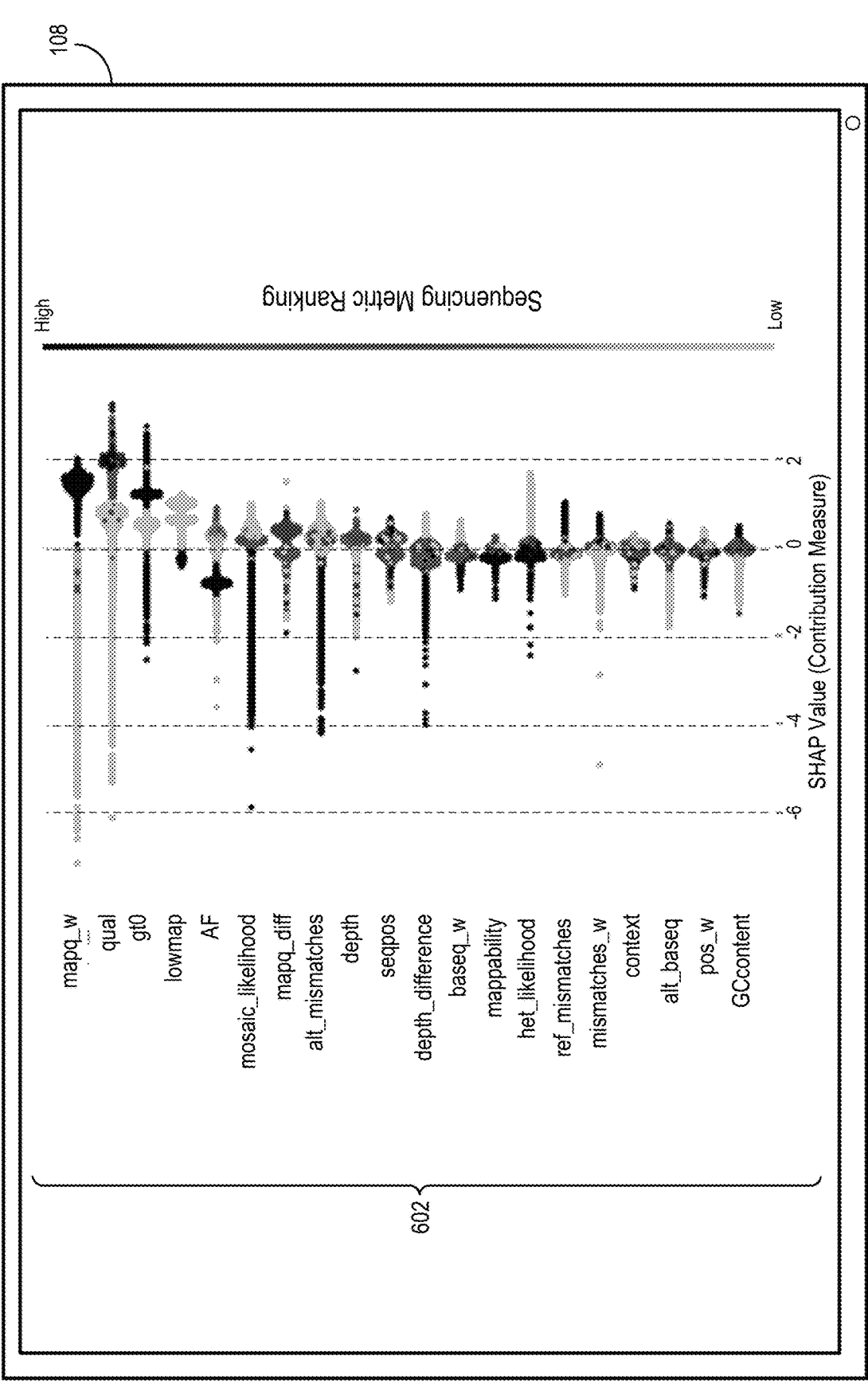
FIG. 6 illustrates an example contribution-measure interface displayed on a client device in accordance with one or more embodiments.

As mentioned above, in certain described embodiments, the base-caller-recalibration system 106 generates and provides contribution measures associated with sequencing metrics. In particular, the base-caller-recalibration system 106 determines respective contribution measures indicating how impactful individual sequencing metrics are in determining a particular nucleotide-base call. FIG. 6 illustrates an example visualization of contribution measures for sequencing metrics associated with a nucleotide-base call in accordance with one or more embodiments.

As illustrated in FIG. 6, the client device 108 displays a contribution-measure interface 602 that includes individual depictions of contribution measures associated with corresponding sequencing metrics. Indeed, the base-caller-recalibration system 106 determines a contribution measure for a sequencing metric based on how impactful or influential the sequencing metric is on a final nucleotide-base call. Unlike many prior systems that utilize deep learning architectures, the structure of the call-generation model used by the base-caller-recalibration system 106 facilitates the determination of such contribution measures on a metric-by-metric basis.

For example, the base-caller-recalibration system 106 determines contribution measures by determining Shapley Additive Explanation (SHAP) values for each of the sequencing metrics for a nucleotide-base call. Specifically, the base-caller-recalibration system 106 determines a SHAP value by determining an impact of a sequencing metric as compared to the results of a baseline value (e.g., a baseline value for the sequencing metric). As shown in FIG. 6, the base-caller-recalibration system 106 determines contribution measures for a number of listed sequencing metrics, where the thicker (e.g., more bulbous) portions of the graphs for each sequencing metric (roughly) indicate its contribution measure.

As further shown in FIG. 6, the base-caller-recalibration system 106 can rank the sequencing metrics according to contribution measures as well. For instance, the base-caller-recalibration system 106 determines that the contribution for the mapq_w metric is highest among those displayed within the contribution-measure interface 602, followed by the qual metric, the gt0 metric, and so forth down the list.

Figure 7A:
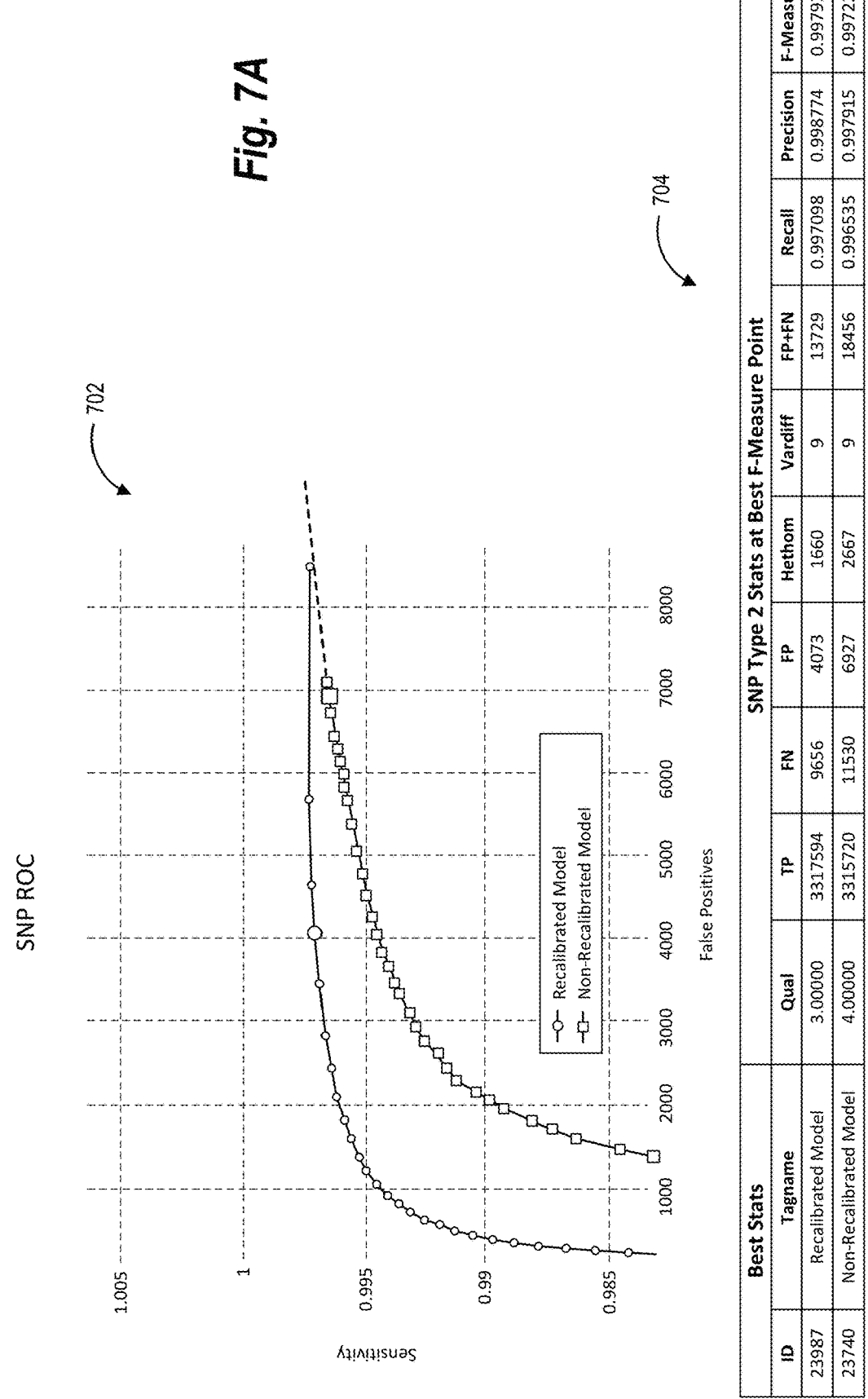
FIGS. 7A-7B illustrate graphs depicting accuracy improvements associated with the base-caller-recalibration system utilizing a call-recalibration-machine-learning model in accordance with one or more embodiments.
Figure 7B:
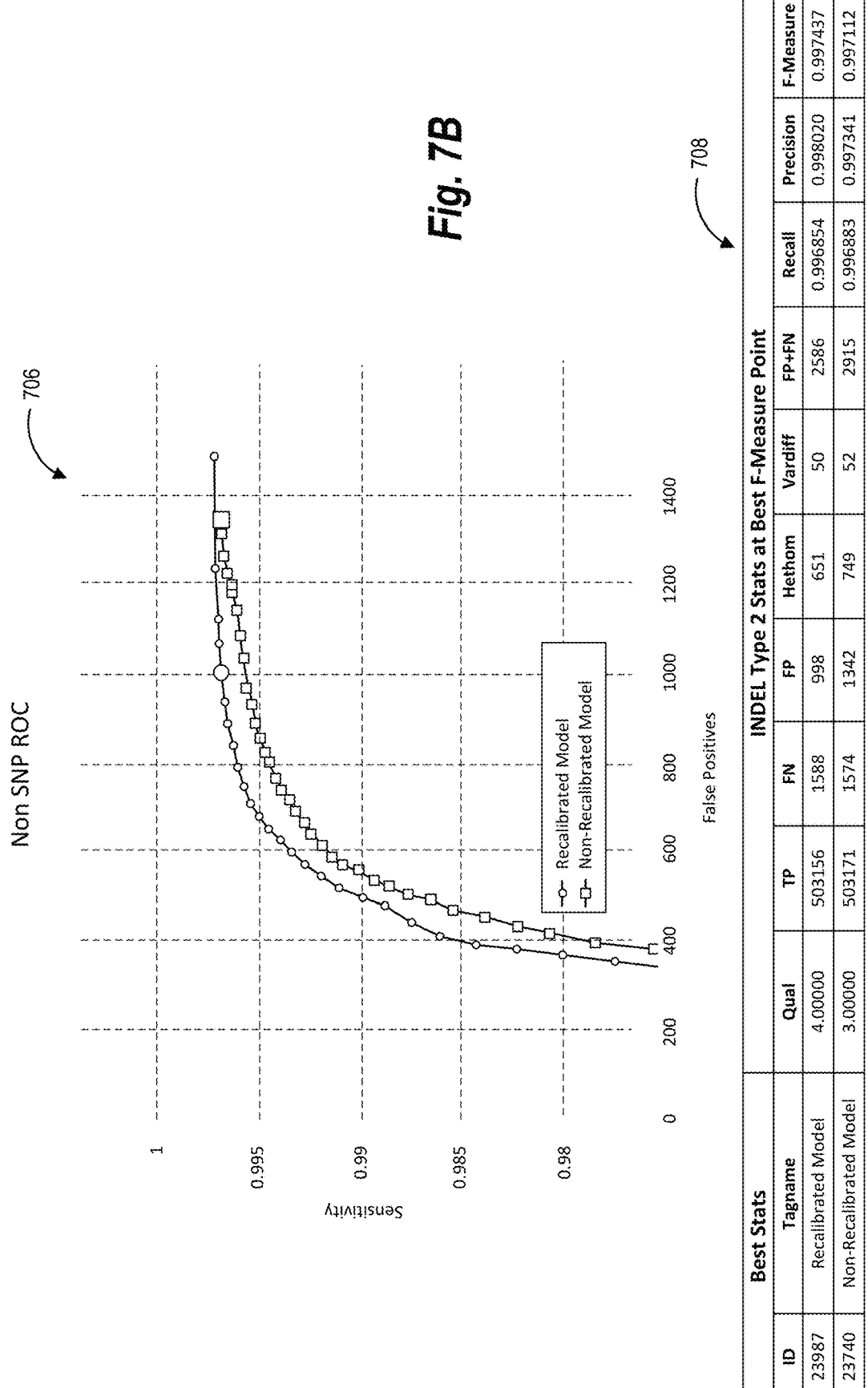

As mentioned above, in certain described embodiments, the base-caller-recalibration system 106 improves in accuracy over prior systems. In particular, the base-caller-recalibration system 106 reduces false positive variant-nucleotide-base calls and false negative variant-nucleotide-base calls compared to prior systems. Indeed, by utilizing a call-recalibration-machine-learning model to recalibrate nucleotide-base calls, the base-caller-recalibration system 106 even improves over previous versions of the call-generation model that did not utilize a call-recalibration-machine-learning model (but which still outperform other systems). FIGS. 7A-7B illustrate graphs depicting the improvements of the base-caller-recalibration system 106 in accordance with one or more embodiments. Specifically, FIG. 7A illustrates improvements for nucleotide-base calls of SNPs while FIG. 7B illustrates improvements for non-SNPs (e.g., indels).

As illustrated in FIG. 7A, a graph 702 includes a receiver operating characteristic (ROC) curve that illustrates reductions in SNP false positives for the base-caller-recalibration system 106 as compared to a system utilizing a call-generation model (e.g., the call-generation model 420) without recalibrating via variant-call classifications by a call-recalibration-machine-learning model. The graph 702 depicts portions of two different ROC curves representing sensitivity over false positive variants detected, where sensitivity represents a number of correctly determined true-positive-variant calls divided by the sum of true-positive-variant calls and false-positive-variant calls. In particular, the graph 702 depicts ROC curves for the base-caller-recalibration system 106 utilizing the call-recalibration-machine-learning model—that is, "Recalibrated Model." The "Recalibrated Model" refers to a call-recalibration-machine-learning model tested using PrecisionFDA HG002 high confidence truth set. Additionally, the graph 702 depicts a sensitivity ROC curve for a call-generation model without a call-recalibration-machine-learning model, that is, "Non-Recalibrated Model." To zoom in on the top of each ROC curve, the y-axis for sensitivity starts around 0.985. At the end of the ROC curve for the "Recalibrated Model," the sensitivity is 0.998.

As shown, the base-caller-recalibration system 106 with the call-recalibration-machine-learning model exhibits approximately a 65% improvement for false positives at certain sensitivities (e.g., as indicated by the left shift of the Recalibrated Model curve as compared to the Non-Recalibrated Model curve at the same y-axis values). As shown in table 704, as another example, at their best measurement points, the base-caller-recalibration system 106 generates only 4,073 false positives, whereas the non-recalibrated system generates 6,972 false positives.

As further depicted in the table 704, the base-caller-recalibration system 106 exhibits other improvements as well. For example, the base-caller-recalibration system 106 generates fewer false negatives and fewer genotype errors (e.g., het/hom errors) than the non-recalibrated system. The base-caller-recalibration system 106 also improves over the non-recalibrated system in recall, precision, and F-measure, all while adding minimally to overall computation time. In particular, by adding a call-recalibration-machine-learning model to a call generation model, the call-recalibration-machine-learning model adds approximately 1 to 5 minutes to generating a variant call file from a sequencing run (e.g., approximately 21 to 25 minutes).

As illustrated in FIG. 7B, a graph 706 includes an ROC curve that illustrates reductions in non-SNP (i.e., indels) false positives for the base-caller-recalibration system 106 as compared to the non-recalibrated version of the call-generation model. Similar to the above discussion, the graph 706 depicts the base-caller-recalibration system 106 utilizing the call-recalibration-machine-learning model ("Recalibrated Model") compared with the "Non-Recalibrated Model." To zoom in on the top of each ROC curve, the y-axis for sensitivity starts around 0.98.

As shown by the graph 706, the base-caller-recalibration system 106 improves in non-SNP false positives at the same sensitivity (e.g., as indicated by larger dots). As shown in a table 708, for example, at their best measurement points, the base-caller-recalibration system 106 generates only 998 false positives at the illustrated sensitivity while the non-recalibrated system generates 1,342 false positives.

As further depicted by the table 708, the base-caller-recalibration system 106 exhibits other improvements over prior systems as well. For example, the base-caller-recalibration system 106 generates fewer genotype errors (e.g., het/hom errors) than the non-recalibrated system. The base-caller-recalibration system 106 also improves over the non-recalibrated system in precision and F-measure for non-SNPs.

Figure 8:
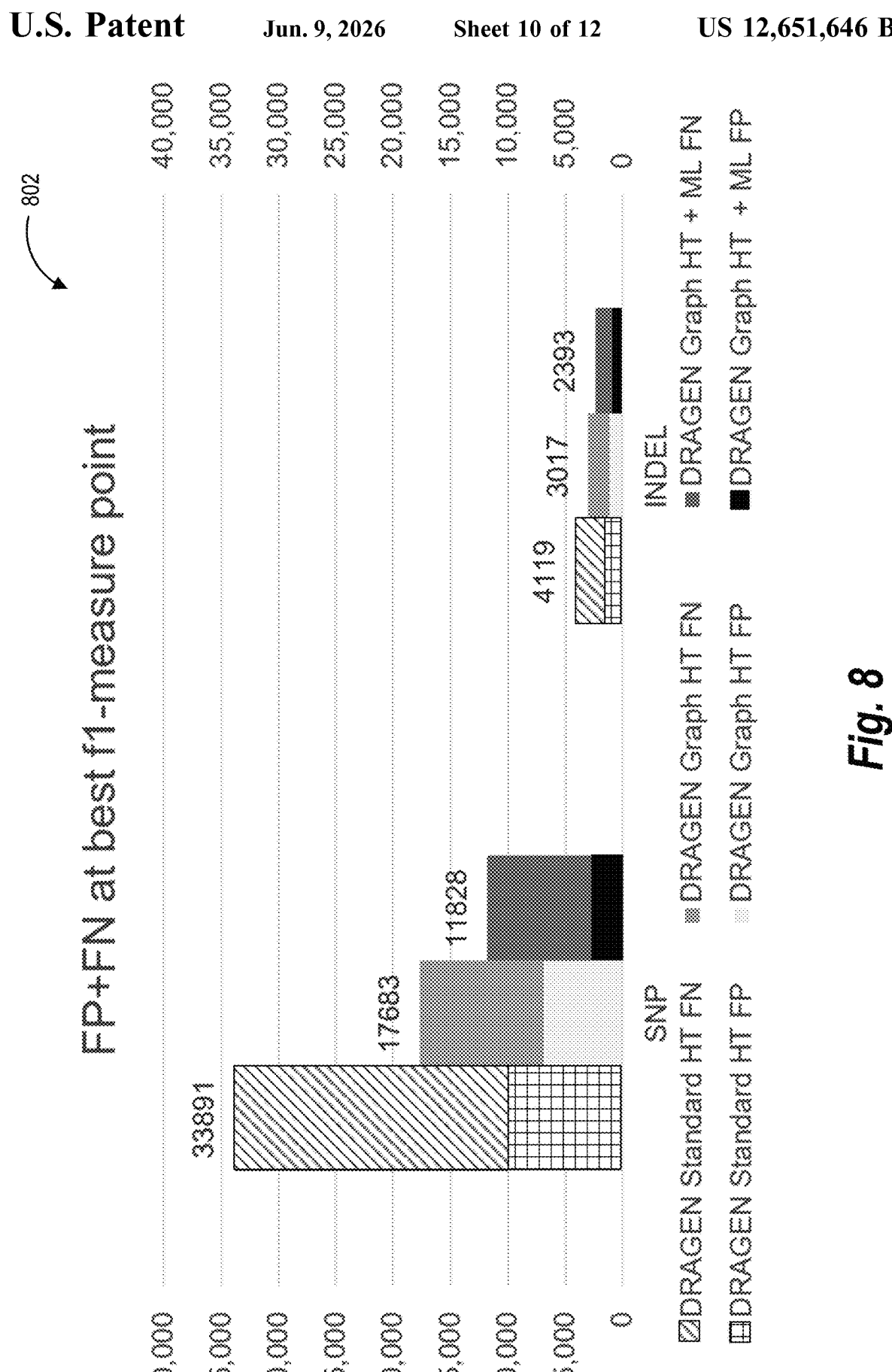
FIG. 8 illustrates a graph comparing the base-caller-recalibration system with non-recalibrated systems in accordance with one or more embodiments.

In addition to the accuracy improvements shown by the ROC curves in FIGS. 7A and 7B, FIG. 8 illustrates a graph 802 that demonstrates improved accuracy by the base-callerrecalibration system 106 over non-calibrated systems. Specifically, the graph 802 depicts false positive variant calls (FP) and false negative variant calls (FN) for the base-caller-recalibration system 106 against those of non-recalibrated systems for both SNPs and indels (e.g., as generated for both standard hash tables (HT) and graph hash tables). As shown, the base-caller-recalibration system 106 greatly reduces the overall FP+FN value at a best F1 score measuring point for standard and graph hash tables for both SNPs and indels. Indeed, the base-caller-recalibration system 106 reduces the number of false positives and the number of false negatives by utilizing a call-recalibration-machine-learning model.

Figure 9:
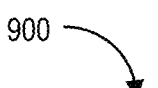
FIG. 9 illustrates a flowchart of a series of acts for generating a nucleotide-base call based on variant-call classifications from a call-recalibration-machine-learning model in accordance with one or more embodiments in accordance with one or more embodiments.
Figure 9:
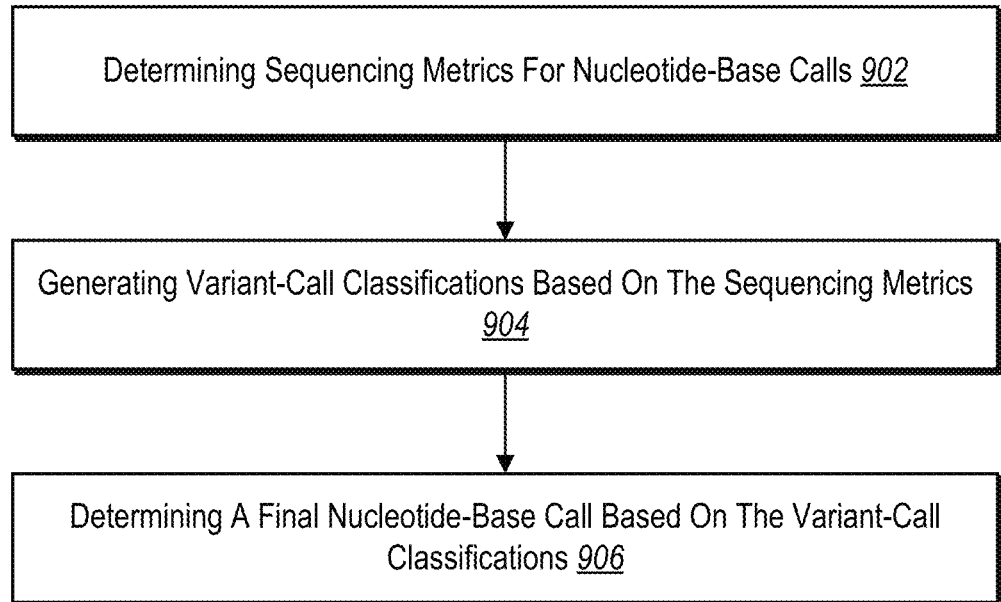

Turning now to FIG. 9, this figure illustrates a flowchart of a series of acts 900 of generating a nucleotide-base call based on variant-call classifications from a call-recalibration-machine-learning model in accordance with one or more embodiments. While FIG. 9 illustrates acts according to one embodiment, alternative embodiments may omit, add to, reorder, and/or modify any of the acts shown in FIG. 9. The acts of FIG. 9 can be performed as part of a method. Alternatively, a non-transitory computer readable storage medium can comprise instructions that, when executed by one or more processors, cause a computing device to perform the acts depicted in FIG. 9. In still further embodiments, a system comprising at least one processor and a non-transitory computer readable medium comprising instructions that, when executed by one or more processors, cause the system to perform the acts of FIG. 9.

As shown in FIG. 9, the acts 900 include an act 902 of determining sequencing metrics for nucleotide-base calls. In particular, the act 902 involves determining sequencing metrics for nucleotide-base calls of nucleotide reads corresponding to a genomic coordinate of a sample nucleotide sequence. For example, the act 902 involves determining one or more of read-based sequencing metrics, call-model-generated sequencing metrics, or externally sourced sequencing metrics. In some cases, determining call-model-generated sequencing metrics involves determining variant-calling sequencing metrics and mapping-and-alignment sequencing metrics from a call-generation model. In certain embodiments, the act 902 involves determining re-engineered sequencing metrics derived from other sequencing metrics for the nucleotide-base calls. The act 902 can also include determining one or more of read-based sequencing metrics comprising metrics derived from the nucleotide reads of the sample nucleotide sequence, call-model-generated sequencing metrics generated via a call-generation model, or externally sourced sequencing metrics identified from one or more external databases.

In addition, the series of acts 900 includes an act 904 of generating variant-call classifications based on the sequencing metrics. In particular, the act 904 involves generating, utilizing a call-recalibration-machine-learning model and based on the sequencing metrics, one or more variant-call classifications indicating an accuracy of identifying a variant at the genomic coordinate. In some embodiments, the series of acts 900 includes an act of modifying one or more data fields corresponding to a variant call file for one or more of call quality, genotype, or genotype quality based on the one or more variant-call classifications. In some cases, the act 904 involves generating one or more of a false-positive classification, a genotype-error classification, or a true-positive classification. The act 904 can involve utilizing the call-recalibration-machine-learning model to generate one or more classifications corresponding to a genotype for the final nucleotide-base call for the genomic coordinate. In some cases, the call-recalibration-machine-learning model comprises one or more of a neural network, a deep-learning transformer, a gradient boost decision tree, a random forest model, a linear regression, a support vector machine, or a logistic regression.

In certain embodiments, the act 904 involves generating the one or more variant-call classifications based on the variant-calling sequencing metrics and the mapping-and-alignment sequencing metrics utilizing the call-recalibration-machine-learning model. The act 904 can also include utilizing a machine-learning classifier to generate one or more of: a false-positive probability that the final nucleotide-base call is a false positive, a genotype-error probability that a genotype for the final nucleotide-base call is incorrect, or a true-positive probability that the final nucleotide-base call is a true positive.

As further illustrated in FIG. 9, the series of acts 900 includes an act 906 of determining a final nucleotide-base call based on the variant-call classifications. In particular, the act 906 involves determining a final nucleotide-base call for the genomic coordinate based on the one or more variant-call classifications. For example, the act 906 involves determining an initial nucleotide-base call for the genomic coordinate utilizing a call-generation model based on one or more sequencing metrics and modifying one or more data fields corresponding to a variant call file and the initial nucleotide-base call based on the one or more variant-call classifications from the call-recalibration-machine-learning model. In some cases, the act 906 involves generating a variant call for the genomic coordinate based on the one or more variant-call classifications. In some embodiments, the act 906 involves determining the final nucleotide-base call as part of a variant call comprising a single nucleotide polymorphism, a deletion, an insertion, or a structural variation corresponding to the genomic coordinate.

Indeed, the act 906 can involve determining the final nucleotide-base call for the genomic coordinate by changing a genotype of an initial nucleotide-base call to an updated genotype of an updated nucleotide-base call. The series of acts 900 can also include acts of updating a base-call-quality metric for the variant call based on the one or more variant-call classifications, determining that the base-call-quality metric for the variant call passes a quality filter, and generating a variant call file comprising the variant call based on the base-call-quality metric passing the quality filter.

In some embodiments, the series of acts 900 includes an act of increasing a base-call-quality metric for the nucleotide-base call based on the one or more variant-call classifications. In these or other embodiments, the series of acts 900 includes an act of determining the increased base-call-quality metric passes a quality filter and generating a variant call file that includes the final nucleotide-base call based on the increased base-call-quality metric or, alternatively, updating a variant call file to include the final nucleotide-base call based on the increased base-call-quality metric. In certain cases, the series of acts 900 includes acts of decreasing a base-call-quality metric for the final nucleotide-base call based on the one or more variant-call classifications, determining that the decreased base-call-quality metric does not pass a quality filter, and generating a post-filter variant call file that excludes the final nucleotide-base call based on the decreased base-call-quality metric not passing the quality filter or, alternatively, updating a variant call file to exclude the final nucleotide-base call based on the decreased base-call-quality metric.

In one or more implementations, the series of acts 900 includes acts of determining contribution measures for the sequencing metrics indicating respective measures of impact that the sequencing metrics have on the final nucleotide-base call and providing, for display on a client device, a visualization of the contribution measures corresponding to one or more of the sequencing metrics.

The methods described herein can be used in conjunction with a variety of nucleic acid sequencing techniques. Particularly applicable techniques are those wherein nucleic acids are attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of a target nucleic acid (i.e., a nucleic-acid polymer) can be an automated process. Preferred embodiments include sequencing-by-synthesis (SBS) techniques.

SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides, as set forth in further detail below. In methods using nucleotide monomers lacking terminators, the number of nucleotides added in each cycle is generally variable and dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.).

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Preferred embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing."

Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons. The nucleic acids to be sequenced can be attached to features in an array and the array can be imaged to capture the chemiluminescent signals that are produced due to incorporation of a nucleotides at the features of the array. An image can be obtained after the array is treated with a particular nucleotide type (e.g., A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in WO 04/018497 and U.S. Pat. No. 7,057,026, the disclosures of which are incorporated herein by reference. This approach is being commercialized by Solexa (now Illumina Inc.), and is also described in WO 91/06678 and WO 07/123,744, each of which is incorporated herein by reference. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

Preferably in reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments, each image will show nucleic acid features that have incorporated nucleotides of a particular type. Different features are present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth below.

In particular embodiments some or all of the nucleotide monomers can include reversible terminators. In such embodiments, reversible terminators/cleavable fluors can include fluor linked to the ribose moiety via a 3' ester linkage (Metzker, Genome Res. 15:1767-1776 (2005), which is incorporated herein by reference). Other approaches have separated the terminator chemistry from the cleavage of the fluorescence label (Ruparel et al., Proc Natl Acad Sci USA 102: 5932-7 (2005), which is incorporated herein by reference in its entirety). Ruparel et al described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluor and effectively reverses the termination. Examples of modified nucleotides are also described in U.S. Pat. Nos. 7,427,673, and 7,057,026, the disclosures of which are incorporated herein by reference in their entireties.

Additional exemplary SBS systems and methods which can be utilized with the methods and systems described herein are described in U.S. Patent Application Publication No. 2007/0166705, U.S. Patent Application Publication No. 2006/0188901, U.S. Pat. No. 7,057,026, U.S. Patent Application Publication No. 2006/0240439, U.S. Patent Application Publication No. 2006/0281109, PCT Publication No. WO 05/065814, U.S. Patent Application Publication No. 2005/0100900, PCT Publication No. WO 06/064199, PCT Publication No. WO 07/010,251, U.S. Patent Application Publication No. 2012/0270305 and U.S. Patent Application Publication No. 2013/0260372, the disclosures of which are incorporated herein by reference in their entireties.

Some embodiments can utilize detection of four different nucleotides using fewer than four different labels. For example, SBS can be performed utilizing methods and systems described in the incorporated materials of U.S. Patent Application Publication No. 2013/0079232. As a first example, a pair of nucleotide types can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc.). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g. dATP having a label that is detected in the first channel when excited by a first excitation wavelength), a second nucleotide type that is detected in a second channel (e.g. dCTP having a label that is detected in the second channel when excited by a second excitation wavelength), a third nucleotide type that is detected in both the first and the second channel (e.g. dTTP having at least one label that is detected in both channels when excited by the first and/or second excitation wavelength) and a fourth nucleotide type that lacks a label that is not, or minimally, detected in either channel (e.g. dGTP having no label).

Further, as described in the incorporated materials of U.S. Patent Application Publication No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can utilize sequencing by ligation techniques. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features are present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be utilized with the methods and systems described herein are described in U.S. Pat. Nos. 6,969,488, 6,172,218, and 6,306,597, the disclosures of which are incorporated herein by reference in their entireties.

Some embodiments can utilize nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis". Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003), the disclosures of which are incorporated herein by reference in their entireties). In such embodiments, the target nucleic acid passes through a nanopore. The nanopore can be a synthetic pore or biological membrane protein, such as $\alpha$-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008), the disclosures of which are incorporated herein by reference in their entireties). Data obtained from nanopore sequencing can be stored, processed and analyzed as set forth herein. In particular, the data can be treated as an image in accordance with the exemplary treatment of optical images and other images that is set forth herein.

Some embodiments can utilize methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414 (each of which is incorporated herein by reference) or nucleotide incorporations can be detected with zero-mode waveguides as described, for example, in U.S. Pat. No. 7,315,019 (which is incorporated herein by reference) and using fluorescent nucleotide analogs and engineered polymerases as described, for example, in U.S. Pat. No. 7,405,281 and U.S. Patent Application Publication No. 2008/0108082 (each of which is incorporated herein by reference). The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008), the disclosures of which are incorporated herein by reference in their entireties). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, CT, a Life Technologies subsidiary) or sequencing methods and systems described in US 2009/0026082 A1; US 2009/0127589 A1; US 2010/0137143 A1; or US 2010/0282617 A1, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail below.

The methods set forth herein can use arrays having features at any of a variety of densities including, for example, at least about 10 features/cm2, 100 features/cm2, 500 features/cm2, 1,000 features/cm2, 5,000 features/cm2, 10,000 features/cm2, 50,000 features/cm2, 100,000 features/cm2, 1,000,000 features/cm2, 5,000,000 features/cm2, or higher.

An advantage of the methods set forth herein is that they provide for rapid and efficient detection of a plurality of target nucleic acid in parallel. Accordingly the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized DNA fragments, the system comprising components such as pumps, valves, reservoirs, fluidic lines and the like. A flow cell can be configured and/or used in an integrated system for detection of target nucleic acids. Exemplary flow cells are described, for example, in US 2010/0111768 A1 and U.S. Ser. No. 13/273,666, each of which is incorporated herein by reference. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, CA) and devices described in U.S. Ser. No. 13/273,666, which is incorporated herein by reference.

The sequencing system described above sequences nucleic-acid polymers present in samples received by a sequencing device. As defined herein, "sample" and its derivatives, is used in its broadest sense and includes any specimen, culture and the like that is suspected of including a target. In some embodiments, the sample comprises DNA, RNA, PNA, LNA, chimeric or hybrid forms of nucleic acids. The sample can include any biological, clinical, surgical, agricultural, atmospheric or aquatic-based specimen containing one or more nucleic acids. The term also includes any isolated nucleic acid sample such a genomic DNA, fresh-frozen or formalin-fixed paraffin-embedded nucleic acid specimen. It is also envisioned that the sample can be from a single individual, a collection of nucleic acid samples from genetically related members, nucleic acid samples from genetically unrelated members, nucleic acid samples (matched) from a single individual such as a tumor sample and normal tissue sample, or sample from a single source that contains two distinct forms of genetic material such as maternal and fetal DNA obtained from a maternal subject, or the presence of contaminating bacterial DNA in a sample that contains plant or animal DNA. In some embodiments, the source of nucleic acid material can include nucleic acids obtained from a newborn, for example as typically used for newborn screening.

The nucleic acid sample can include high molecular weight material such as genomic DNA (gDNA). The sample can include low molecular weight material such as nucleic acid molecules obtained from FFPE or archived DNA samples. In another embodiment, low molecular weight material includes enzymatically or mechanically fragmented DNA. The sample can include cell-free circulating DNA. In some embodiments, the sample can include nucleic acid molecules obtained from biopsies, tumors, scrapings, swabs, blood, mucus, urine, plasma, semen, hair, laser capture micro-dissections, surgical resections, and other clinical or laboratory obtained samples. In some embodiments, the sample can be an epidemiological, agricultural, forensic or pathogenic sample. In some embodiments, the sample can include nucleic acid molecules obtained from an animal such as a human or mammalian source. In another embodiment, the sample can include nucleic acid molecules obtained from a non-mammalian source such as a plant, bacteria, virus or fungus. In some embodiments, the source of the nucleic acid molecules may be an archived or extinct sample or species.

Further, the methods and compositions disclosed herein may be useful to amplify a nucleic acid sample having low-quality nucleic acid molecules, such as degraded and/or fragmented genomic DNA from a forensic sample. In one embodiment, forensic samples can include nucleic acids obtained from a crime scene, nucleic acids obtained from a missing persons DNA database, nucleic acids obtained from a laboratory associated with a forensic investigation or include forensic samples obtained by law enforcement agencies, one or more military services or any such personnel. The nucleic acid sample may be a purified sample or a crude DNA containing lysate, for example derived from a buccal swab, paper, fabric or other substrate that may be impregnated with saliva, blood, or other bodily fluids. As such, in some embodiments, the nucleic acid sample may comprise low amounts of, or fragmented portions of DNA, such as genomic DNA. In some embodiments, target sequences can be present in one or more bodily fluids including but not limited to, blood, sputum, plasma, semen, urine and serum. In some embodiments, target sequences can be obtained from hair, skin, tissue samples, autopsy or remains of a victim. In some embodiments, nucleic acids including one or more target sequences can be obtained from a deceased animal or human. In some embodiments, target sequences can include nucleic acids obtained from non-human DNA such a microbial, plant or entomological DNA. In some embodiments, target sequences or amplified target sequences are directed to purposes of human identification. In some embodiments, the disclosure relates generally to methods for identifying characteristics of a forensic sample. In some embodiments, the disclosure relates generally to human identification methods using one or more target specific primers disclosed herein or one or more target specific primers designed using the primer design criteria outlined herein. In one embodiment, a forensic or human identification sample containing at least one target sequence can be amplified using any one or more of the target-specific primers disclosed herein or using the primer criteria outlined herein.

The components of the base-caller-recalibration system 106 can include software, hardware, or both. For example, the components of the base-caller-recalibration system 106 can include one or more instructions stored on a computer-readable storage medium and executable by processors of one or more computing devices (e.g., the client device 108). When executed by the one or more processors, the computer-executable instructions of the base-caller-recalibration system 106 can cause the computing devices to perform the bubble detection methods described herein. Alternatively, the components of the base-caller-recalibration system 106 can comprise hardware, such as special purpose processing devices to perform a certain function or group of functions. Additionally, or alternatively, the components of the base-caller-recalibration system 106 can include a combination of computer-executable instructions and hardware.

Furthermore, the components of the base-caller-recalibration system 106 performing the functions described herein with respect to the base-caller-recalibration system 106 may, for example, be implemented as part of a stand-alone application, as a module of an application, as a plug-in for applications, as a library function or functions that may be called by other applications, and/or as a cloud-computing model. Thus, components of the base-caller-recalibration system 106 may be implemented as part of a stand-alone application on a personal computing device or a mobile device. Additionally, or alternatively, the components of the base-caller-recalibration system 106 may be implemented in any application that provides sequencing services including, but not limited to Illumina BaseSpace, Illumina DRAGEN, or Illumina TruSight software. "Illumina," "BaseSpace," "DRAGEN," and "TruSight," are either registered trademarks or trademarks of Illumina, Inc. in the United States and/or other countries.

Embodiments of the present disclosure may comprise or utilize a special purpose or general-purpose computer including computer hardware, such as, for example, one or more processors and system memory, as discussed in greater detail below. Embodiments within the scope of the present disclosure also include physical and other computer-readable media for carrying or storing computer-executable instructions and/or data structures. In particular, one or more of the processes described herein may be implemented at least in part as instructions embodied in a non-transitory computer-readable medium and executable by one or more computing devices (e.g., any of the media content access devices described herein). In general, a processor (e.g., a microprocessor) receives instructions, from a non-transitory computer-readable medium, (e.g., a memory, etc.), and executes those instructions, thereby performing one or more processes, including one or more of the processes described herein.

Computer-readable media can be any available media that can be accessed by a general purpose or special purpose computer system. Computer-readable media that store computer-executable instructions are non-transitory computer-readable storage media (devices). Computer-readable media that carry computer-executable instructions are transmission media. Thus, by way of example, and not limitation, embodiments of the disclosure can comprise at least two distinctly different kinds of computer-readable media: non-transitory computer-readable storage media (devices) and transmission media.

Non-transitory computer-readable storage media (devices) includes RAM, ROM, EEPROM, CD-ROM, solid state drives (SSDs) (e.g., based on RAM), Flash memory, phase-change memory (PCM), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures can be transferred automatically from transmission media to non-transitory computer-readable storage media (devices) (or vice versa). For example, computer-executable instructions or data structures received over a network or data link can be buffered in RAM within a network interface module (e.g., a NIC), and then eventually transferred to computer system RAM and/or to less volatile computer storage media (devices) at a computer system. Thus, it should be understood that non-transitory computer-readable storage media (devices) can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. In some embodiments, computer-executable instructions are executed on a general-purpose computer to turn the general-purpose computer into a special purpose computer implementing elements of the disclosure. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Embodiments of the present disclosure can also be implemented in cloud computing environments. In this description, "cloud computing" is defined as a model for enabling on-demand network access to a shared pool of configurable computing resources. For example, cloud computing can be employed in the marketplace to offer ubiquitous and convenient on-demand access to the shared pool of configurable computing resources. The shared pool of configurable computing resources can be rapidly provisioned via virtualization and released with low management effort or service provider interaction, and then scaled accordingly.

A cloud-computing model can be composed of various characteristics such as, for example, on-demand self-service, broad network access, resource pooling, rapid elasticity, measured service, and so forth. A cloud-computing model can also expose various service models, such as, for example, Software as a Service (SaaS), Platform as a Service (PaaS), and Infrastructure as a Service (IaaS). A cloud-computing model can also be deployed using different deployment models such as private cloud, community cloud, public cloud, hybrid cloud, and so forth. In this description and in the claims, a "cloud-computing environment" is an environment in which cloud computing is employed.

Figure 10:
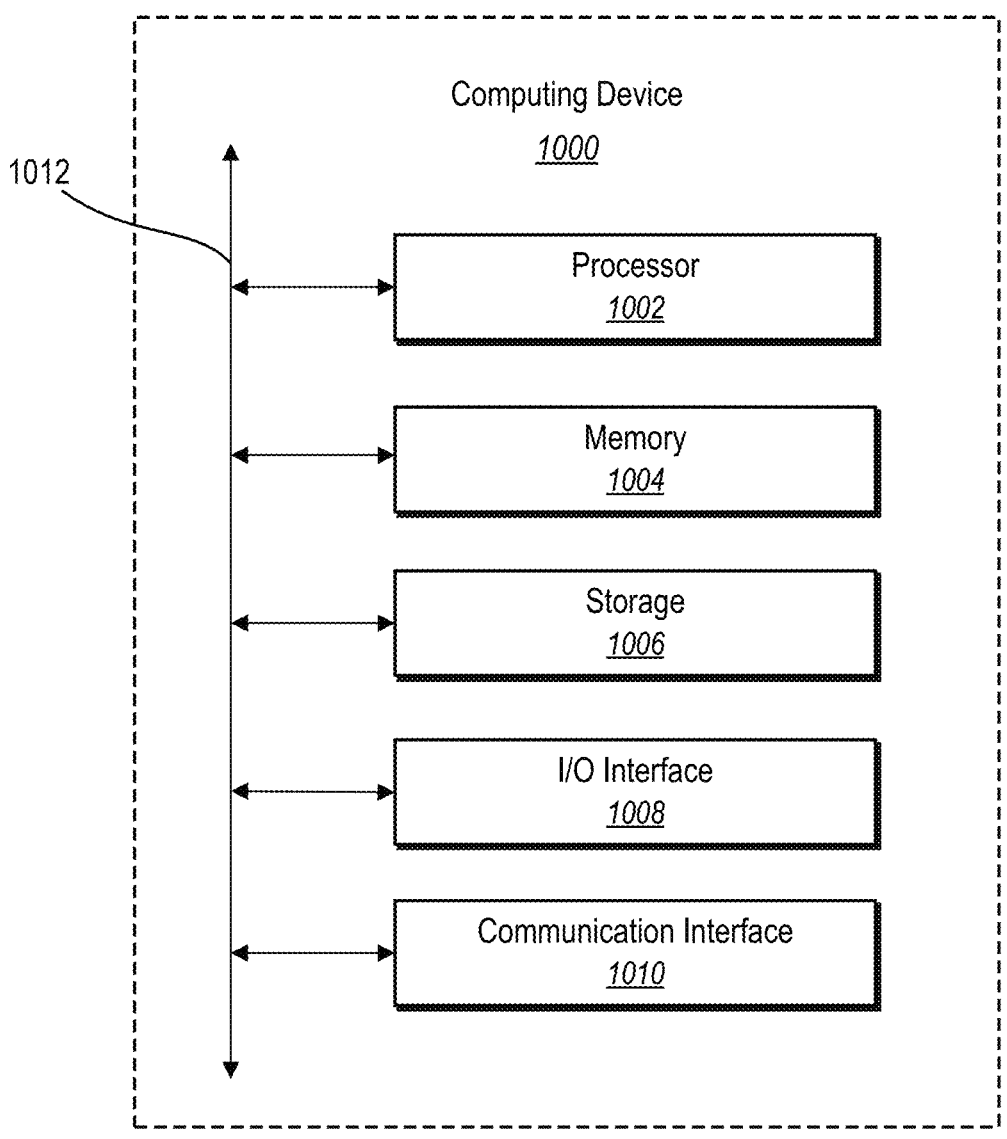
FIG. 10 illustrates a block diagram of an example computing device for implementing one or more embodiments of the present disclosure.

FIG. 10 illustrates a block diagram of a computing device 1000 that may be configured to perform one or more of the processes described above. One will appreciate that one or more computing devices such as the computing device 1000 may implement the base-caller-recalibration system 106 and the sequencing system 104. As shown by FIG. 10, the computing device 1000 can comprise a processor 1002, a memory 1004, a storage device 1006, an I/O interface 1008, and a communication interface 1010, which may be communicatively coupled by way of a communication infrastructure 1012. In certain embodiments, the computing device 1000 can include fewer or more components than those shown in FIG. 10. The following paragraphs describe components of the computing device 1000 shown in FIG. 10 in additional detail.

In one or more embodiments, the processor 1002 includes hardware for executing instructions, such as those making up a computer program. As an example, and not by way of limitation, to execute instructions for dynamically modifying workflows, the processor 1002 may retrieve (or fetch) the instructions from an internal register, an internal cache, the memory 1004, or the storage device 1006 and decode and execute them. The memory 1004 may be a volatile or non-volatile memory used for storing data, metadata, and programs for execution by the processor(s). The storage device 1006 includes storage, such as a hard disk, flash disk drive, or other digital storage device, for storing data or instructions for performing the methods described herein.

The I/O interface 1008 allows a user to provide input to, receive output from, and otherwise transfer data to and receive data from computing device 1000. The I/O interface 1008 may include a mouse, a keypad or a keyboard, a touch screen, a camera, an optical scanner, network interface, modem, other known I/O devices or a combination of such I/O interfaces. The I/O interface 1008 may include one or more devices for presenting output to a user, including, but not limited to, a graphics engine, a display (e.g., a display screen), one or more output drivers (e.g., display drivers), one or more audio speakers, and one or more audio drivers. In certain embodiments, the I/O interface 1008 is configured to provide graphical data to a display for presentation to a user. The graphical data may be representative of one or more graphical user interfaces and/or any other graphical content as may serve a particular implementation.

The communication interface 1010 can include hardware, software, or both. In any event, the communication interface 1010 can provide one or more interfaces for communication (such as, for example, packet-based communication) between the computing device 1000 and one or more other computing devices or networks. As an example, and not by way of limitation, the communication interface 1010 may include a network interface controller (NIC) or network adapter for communicating with an Ethernet or other wire-based network or a wireless NIC (WNIC) or wireless adapter for communicating with a wireless network, such as a WI-FI.

Additionally, the communication interface 1010 may facilitate communications with various types of wired or wireless networks. The communication interface 1010 may also facilitate communications using various communication protocols. The communication infrastructure 1012 may also include hardware, software, or both that couples components of the computing device 1000 to each other. For example, the communication interface 1010 may use one or more networks and/or protocols to enable a plurality of computing devices connected by a particular infrastructure to communicate with each other to perform one or more aspects of the processes described herein. To illustrate, the sequencing process can allow a plurality of devices (e.g., a client device, sequencing device, and server device(s)) to exchange information such as sequencing data and error notifications.

In the foregoing specification, the present disclosure has been described with reference to specific exemplary embodiments thereof. Various embodiments and aspects of the present disclosure(s) are described with reference to details discussed herein, and the accompanying drawings illustrate the various embodiments. The description above and drawings are illustrative of the disclosure and are not to be construed as limiting the disclosure. Numerous specific details are described to provide a thorough understanding of various embodiments of the present disclosure.

The present disclosure may be embodied in other specific forms without departing from its spirit or essential characteristics. The described embodiments are to be considered in all respects only as illustrative and not restrictive. For example, the methods described herein may be performed with less or more steps/acts or the steps/acts may be performed in differing orders. Additionally, the steps/acts described herein may be repeated or performed in parallel with one another or in parallel with different instances of the same or similar steps/acts. The scope of the present application is, therefore, indicated by the appended claims rather than by the foregoing description. All changes that come within the meaning and range of equivalency of the claims are to be embraced within their scope.

We claim:

1. A system comprising:
   at least one processor; and
   a non-transitory computer readable medium comprising instructions that, when executed by the at least one processor, cause the system to:
      determine, utilizing a call-generation model, an initial genotype call indicating a first genotype with respect to a reference genome at a genomic coordinate of a sample nucleotide sequence;
      determine sequencing metrics for the initial genotype call based on nucleotide-base calls of nucleotide reads corresponding to the genomic coordinate of the sample nucleotide sequence;
      generate, utilizing a call-recalibration-machine-learning model running in parallel with the call-generation model to process the sequencing metrics for the initial genotype call, one or more variant-call classifications indicating a probability of a variant call or a non-variant call, with respect to the reference genome, being accurate in individual genotype calls at the genomic coordinate; and
      determine, for the genomic coordinate based on the one or more variant-call classifications, a final genotype call that changes the first genotype of the initial genotype call to a second genotype.

2. The system of claim 1, further comprising instructions that, when executed by the at least one processor, cause the system to:
   increase a base-call-quality metric for the final genotype call based on the one or more variant-call classifications;
   determine the increased base-call-quality metric passes a quality filter; and
   generate a variant call file that includes the final genotype call based on the increased base-call-quality metric.

3. The system of claim 1, further comprising instructions that, when executed by the at least one processor, cause the system to:
   decrease a base-call-quality metric for the final genotype call based on the one or more variant-call classifications;
   determine that the decreased base-call-quality metric does not pass a quality filter; and
   generate a post-filter variant call file that excludes the final genotype call based on the decreased base-call-quality metric not passing the quality filter.

4. The system of claim 1, further comprising instructions that, when executed by the at least one processor, cause the system to determine the final genotype call for the genomic coordinate by:
   determining the initial genotype call for the genomic coordinate utilizing the call-generation model based on one or more sequencing metrics; and
   modifying one or more data fields corresponding to a variant call file and the initial genotype call based on the one or more variant-call classifications from the call-recalibration-machine-learning model.

5. The system of claim 1, further comprising instructions that, when executed by the at least one processor, cause the system to modify one or more data fields corresponding to a variant call file for one or more of call quality, genotype, or genotype quality based on the one or more variant-call classifications.

6. The system of claim 1, further comprising instructions that, when executed by the at least one processor, cause the system to determine the sequencing metrics for the initial genotype call based on the nucleotide-base calls by determining one or more of read-based sequencing metrics, call-model-generated sequencing metrics, or externally sourced sequencing metrics.

7. The system of claim 6, further comprising instructions that, when executed by the at least one processor, cause the system to determine the call-model-generated sequencing metrics by determining variant-caller sequencing metrics and mapping-and-alignment sequencing metrics from the call-generation model.

8. The system of claim 1, further comprising instructions that, when executed by the at least one processor, cause the system to determine the sequencing metrics for the initial genotype call based on the nucleotide-base calls by determining re-engineered sequencing metrics derived from other sequencing metrics for the nucleotide-base calls.

9. The system of claim 1, further comprising instructions that, when executed by the at least one processor, cause the system to generate the one or more variant-call classifications by generating one or more of a false-positive classification, a genotype-error classification, or a true-positive classification.

10. The system of claim 1, further comprising instructions that, when executed by the at least one processor, cause the system to:

determine the initial genotype call by determining, utilizing the call-generation model to process one or more read-based sequencing metrics derived from the nucleotide reads of the sample nucleotide sequence, the initial genotype call; and generate the one or more variant-call classifications by generating, utilizing the call-recalibration-machine-learning model in parallel with the call-generation model to process the one or more read-based sequencing metrics, one or more probabilities of the initial genotype call being accurate at the genomic coordinate.

11. A non-transitory computer readable medium comprising instructions that, when executed by at least one processor, cause a computing device to:

determine, utilizing a call-generation model, an initial genotype call indicating a first genotype with respect to a reference genome at a genomic coordinate of a sample nucleotide sequence;

determine sequencing metrics for the initial genotype call based on nucleotide-base calls of nucleotide reads corresponding to the genomic coordinate of the sample nucleotide sequence;

generate, utilizing a call-recalibration-machine-learning model running in parallel with the call-generation model to process the sequencing metrics for the initial genotype call, one or more variant-call classifications indicating a probability of a variant call or non-variant call, with respect to the reference genome, being accurate in individual genotype calls at the genomic coordinate; and determine, for the genomic coordinate based on the one or more variant-call classifications, a final genotype call that changes the first genotype of the initial genotype call to a second genotype.

12. The non-transitory computer readable medium of claim 11, further comprising instructions that, when executed by the at least one processor, cause the computing device to determine the final genotype call as part of a variant call comprising a single nucleotide polymorphism, a deletion, or an insertion corresponding to the genomic coordinate.

13. The non-transitory computer readable medium of claim 11, further comprising instructions that, when executed by the at least one processor, cause the computing device to determine the final genotype call for the genomic coordinate by changing a genotype of the initial genotype call to an updated genotype of an updated genotype call.

14. The non-transitory computer readable medium of claim 11, further comprising instructions that, when executed by the at least one processor, cause the computing device to generate the one or more variant-call classifications by utilizing the call-recalibration-machine-learning model to generate one or more classifications corresponding to a genotype for the final genotype call for the genomic coordinate.

15. The non-transitory computer readable medium of claim 11, further comprising instructions that, when executed by the at least one processor, cause the computing device to:

determine the sequencing metrics by determining variant-caller sequencing metrics and mapping-and-alignment sequencing metrics from the call-generation model; and generate, utilizing the call-recalibration-machine-learning model in parallel with the call-generation model to process the variant-caller sequencing metrics and the mapping-and-alignment sequencing metrics, the one or more variant-call classifications.

16. A computer-implemented method comprising:

determining, utilizing a call-generation model, an initial genotype call indicating a first genotype with respect to a reference genome at a genomic coordinate of a sample nucleotide sequence;

determining sequencing metrics for the initial genotype call based on nucleotide-base calls of nucleotide reads corresponding to the genomic coordinate of the sample nucleotide sequence;

generating, utilizing a call-recalibration-machine-learning model running in parallel with the call-generation model to process the sequencing metrics for the initial genotype call, one or more variant-call classifications indicating a probability of a variant call or non-variant call, with respect to the reference genome, being accurate in individual genotype calls at the genomic coordinate; and determining, for the genomic coordinate based on the one or more variant-call classifications, a final genotype call that changes the first genotype of the initial genotype call to a second genotype.

17. The computer-implemented method of claim 16, further comprising:

updating a base-call-quality metric for the variant call based on the one or more variant-call classifications;

determining that the base-call-quality metric for the variant call passes a quality filter; and generating a variant call file comprising the variant call based on the base-call-quality metric passing the quality filter.

18. The computer-implemented method of claim 16, wherein generating the one or more variant-call classifications comprises utilizing a machine-learning classifier to generate one or more of:

a false-positive probability that the initial genotype call is a false positive;

a genotype-error probability that a genotype for the initial genotype call is incorrect; or a true-positive probability that the initial genotype call is a true positive.

19. The computer-implemented method of claim 16, wherein determining the sequencing metrics comprises determining one or more of read-based sequencing metrics comprising metrics derived from the nucleotide reads of the sample nucleotide sequence, call-model-generated sequencing metrics generated via the call-generation model, or externally sourced sequencing metrics identified from one or more external databases.

20. The computer-implemented method of claim 16, further comprising determining contribution measures for the sequencing metrics indicating respective measures of impact that the sequencing metrics have on the initial genotype call for the genomic coordinate.

21. The computer-implemented method of claim 16, wherein the call-recalibration-machine-learning model comprises one or more of a neural network, a gradient boost decision tree, a random forest model, a support vector machine, a linear regression, or a logistic regression.

* * * * *